United States Patent
Dinsmoor et al.

(10) Patent No.: US 7,654,985 B2
(45) Date of Patent: Feb. 2, 2010

(54) CONTROLLED DETACHMENT OF INTRA-LUMINAL MEDICAL DEVICE

(75) Inventors: David A. Dinsmoor, St. Paul, MN (US); Mark A. Christopherson, Shoreview, MN (US)

(73) Assignee: Given Imaging Ltd., Yoqneam (IL)

( * ) Notice: Subject to any disclaimer, the term of this patent is extended or adjusted under 35 U.S.C. 154(b) by 210 days.

(21) Appl. No.: 10/813,307

(22) Filed: Mar. 30, 2004

(65) Prior Publication Data

US 2005/0222537 A1 Oct. 6, 2005

(51) Int. Cl.
*A61B 5/05* (2006.01)
*A61M 5/32* (2006.01)

(52) U.S. Cl. ........................ 604/174; 600/350
(58) Field of Classification Search ......... 604/174–178, 604/164.04; 600/350; 607/40
See application file for complete search history.

(56) References Cited

U.S. PATENT DOCUMENTS

| | | | | |
|---|---|---|---|---|
| 3,844,272 A | * | 10/1974 | Banko | 600/566 |
| 5,247,938 A | * | 9/1993 | Silverstein et al. | 600/459 |
| 5,883,625 A | | 3/1999 | Crawford et al. | |
| 5,967,986 A | * | 10/1999 | Cimochowski et al. | 600/454 |
| 6,021,352 A | * | 2/2000 | Christopherson et al. | 607/42 |
| 6,285,897 B1 | | 9/2001 | Kilcoyne et al. | |
| 6,535,764 B2 | * | 3/2003 | Imran et al. | 607/40 |
| 6,689,056 B1 | * | 2/2004 | Kilcoyne et al. | 600/300 |
| 6,754,536 B2 | | 6/2004 | Swoyer et al. | |
| 7,020,531 B1 | * | 3/2006 | Colliou et al. | 607/133 |
| 7,175,660 B2 | * | 2/2007 | Cartledge et al. | 623/2.11 |
| 2004/0260346 A1 | * | 12/2004 | Overall et al. | 607/4 |
| 2005/0060030 A1 | * | 3/2005 | Lashinski et al. | 623/2.37 |
| 2005/0209653 A1 | | 9/2005 | Herbert et al. | |

* cited by examiner

*Primary Examiner*—Kevin C. Sirmons
*Assistant Examiner*—Andrew M Gilbert
(74) *Attorney, Agent, or Firm*—Pearl Cohen Zedek Latzer, LLP

(57) ABSTRACT

An intra-luminal medical device includes a fixation mechanism to attach the medical device to tissue within a body lumen, and a detachment mechanism to permit selective detachment of the medical device from the tissue attachment site without the need for endoscopic or surgical intervention. An electromagnetic device may be provided to mechanically actuate the detachment mechanism. Alternatively, a fuse link may be electrically blown to detach the medical device. As a further alternative, a rapidly degradable bonding agent may be exposed to a degradation agent to detach the medical device from a bonding surface within the body lumen. The medical device may eliminate problems associated with uncertain and inconsistent detachment of intra-luminal medical devices.

24 Claims, 16 Drawing Sheets

CONTROLLED DETACHMENT OF INTRA-LUMINAL MEDICAL DEVICE

FIELD OF THE INVENTION

The invention relates to medical devices for temporary deployment in a body lumen and, more particularly, techniques for attachment and detachment of intra-luminal medical devices.

BACKGROUND

Gastroesophageal reflux occurs when stomach fluid, which typically includes stomach acids, intermittently flows from the stomach into the esophagus. It is common for most people to experience this fluid reflux occasionally as heartburn. Gastroesophageal reflux disease (GERD) is a clinical condition in which the reflux of stomach fluid into the esophagus is frequent enough and severe enough to impact a patient's normal functioning or to cause damage to the esophagus.

In the lower part of the esophagus, where the esophagus meets the stomach, there is a muscular valve called the lower esophageal sphincter (LES). Normally, the LES relaxes to allow food to enter into the stomach from the esophagus. The LES then contracts to prevent stomach fluids from entering the esophagus. In GERD, the LES relaxes too frequently or at inappropriate times, allowing stomach fluids to reflux into the esophagus.

The most common symptom of GERD is heartburn. Acid reflux may also lead to esophageal inflammation, which causes symptoms such as painful swallowing and difficulty swallowing. Pulmonary symptoms such as coughing, wheezing, asthma, or inflammation of the vocal cords or throat may occur in some patients. More serious complications from GERD include esophageal ulcers and narrowing of the esophagus. The most serious complication from chronic GERD is a condition called Barrett's esophagus in which the epithelium of the esophagus is replaced with abnormal tissue. Barrett's esophagus is a risk factor for the development of cancer of the esophagus.

Accurate diagnosis of GERD is difficult but important. Accurate diagnosis allows identification of individuals at high risk for developing the complications associated with GERD. It is also important to be able to differentiate between gastroesophageal reflux, other gastrointestinal conditions, and various cardiac conditions. For example, the similarity between the symptoms of a heart attack and heartburn often lead to confusion about the cause of the symptoms.

Esophageal manometry, esophageal endoscopy, and esophageal pH monitoring are standard methods of measuring esophageal exposure to stomach acids and are currently used to diagnose GERD. A variety of endoscopic devices have been designed to monitor various parameters within the esophagus. Many devices require an indwelling catheter to maintain a sensor in place within the esophagus. The catheter protrudes from the patient's nasal or oral passage, however, causing discomfort and ordinarily requiring in-patient supervision.

The Bravo™ pH monitoring system, commercially available from Medtronic, Inc., of Minneapolis, Minn., is an example of a system useful in diagnosing esophageal reflux without the need for a catheter. The Bravo system includes an intra-luminal capsule that is temporarily placed within the esophagus via an endoscopic delivery device. The capsule has a vacuum cavity that captures a portion of the esophageal mucosal tissue. A physician then advances a pin through the captured tissue to secure the capsule relative to the esophageal wall. The capsule causes little discomfort and permits the patient to ambulate. Eventually, the capture tissue sloughs away and releases the capsule, which then passes through the patient's gastrointestinal tract for eventual discharge.

Table 1 below lists documents that disclose various techniques for diagnosing or detecting GERD, and other documents that disclose techniques for measuring conditions within the esophagus.

TABLE 1

| Patent Number | Inventors | Title |
| --- | --- | --- |
| 5,833,625 | Essen-Moller | Ambulatory Reflux Monitoring System |
| 5,967,986 | Cimochowski et al. | Endoluminal Implant with Fluid Flow Sensing Capability |
| 6,285,897 | Kilcoyne et al. | Remote Physiological Monitoring System |
| 6,689,056 | Kilcoyne et al. | Implantable Monitoring Probe |
| US20020103424 | Swoyer et al. | Implantable medical device affixed internally within the gastrointestinal tract |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the techniques of the present invention.

SUMMARY OF THE INVENTION

In general, the invention is directed to techniques for controlled detachment of intra-luminal medical devices such as capsule-like devices carrying sensors, electrical stimulators, therapeutic substances, or the like. A medical device in accordance with the invention incorporates a controlled detachment mechanism to selectively detach a medical device from a tissue attachment site within a body lumen.

Various embodiments of the present invention provide solutions to one or more problems existing in the prior art with respect to prior devices for intra-luminal sensing and stimulation. These problems include the inability of existing intra-luminal medical devices to be selectively detached when desired. Intra-luminal medical devices such as capsules generally do not permit on-demand detachment without endoscopic or surgical intervention. On the contrary, detachment typically occurs when tissue at the attachment site sloughs away, or when degradable attachment material carried by the medical device is sufficiently degraded. Consequently, the time of detachment, and hence the duration of attachment, can be uncertain. In particular, an intra-luminal medical device may reside at the attachment site for an undesirably long period of time. For example, a medical device may acquire sufficient data or deliver a sufficient course of therapy, yet still remain in place for a prolonged period of time. In some cases, removal of the medical device may require endoscopic or surgical intervention. In other cases, an intra-luminal medical device may release too quickly due to differences in tissue integrity or other attachment conditions, preventing a sufficient amount of time for monitoring or therapy.

Various embodiments of the present invention are capable of solving at least one of the foregoing problems. When embodied in a device for intra-luminal monitoring or stimulation, for example, the invention includes a variety of features that facilitate the controlled detachment of such a device without the need for endoscopic or surgical intervention. In particular, the invention provides features that permit self-detachment of an intra-luminal device. Detachment may occur at a desired time in response to a control signal, and need not rely on tissue integrity or other attachment conditions. The control signal may be generated on-demand by a user or automatically in response to expiration of a timer or upon performance of a sufficient course of monitoring or stimulation. In this manner, the invention incorporates features that permit an intra-luminal medical device to be placed within a body lumen for a controllable amount of time for monitoring, therapy, or both. Accordingly, a medical device configured in accordance with the invention may eliminate one or more of the problems that can result from uncertain and inconsistent detachment of intra-luminal medical devices Various embodiments of the invention may possess one or more features to solve the aforementioned problems in the existing art. In some embodiments, a medical device for placement within a body lumen of a patient comprises a device housing, a fixation mechanism and a detachment mechanism. The device housing is sized for introduction into the body lumen. The fixation mechanism attaches the device housing to a surface within the body lumen. The detachment mechanism detaches the device housing from the surface of the body lumen. The detachment mechanism may be responsive to a control signal to detach the medical device from a tissue site.

As an example, an intra-luminal device may be equipped with a fixation mechanism having a spring-loaded shaft to capture tissue at an attachment site. In this example, the spring bias forces the shaft toward the tissue, e.g., to pinch or penetrate the tissue. However, an actuator, such as an electromagnetic device, is provided to selectively drive the shaft against the spring bias and thereby release the tissue. Examples of a suitable electromagnetic device include a solenoid coil.

As an alternative, the spring bias may force the shaft away from the tissue. In this case, a piezoelectric element or other actuator may be provided with a detent that abuts one end of the shaft, and holds the shaft against the spring bias to engage the tissue. Upon activation of the piezoelectric element, the detent clears the shaft, permitting the shaft to release the tissue.

As a further example, the shaft may include a fuse link that is electrically blowable to sever the shaft. Upon activation of a current source to drive current through the shaft, the link disintegrates and permits the capsule to release from the tissue.

As an added example, the fixation mechanism may include a bonding agent that bonds the medical device to the tissue site. The bonding agent may be biodegradable or rapidly degradable in the presence of a degradation agent, permitting detachment of the medical device upon application of the degradation agent to the tissue site.

In comparison to known techniques for electrical stimulation of the gastrointestinal tract, various embodiments of the invention may provide one or more advantages. For example, the invention permits self-detachment of an intra-luminal medical device at a desired time. In this manner, the invention supports on-demand or timed detachment of an intra-luminal medical device without the need for endoscopic or surgical intervention. Consequently, the time of detachment can be controlled, providing greater certainty about the duration of attachment, and hence the duration of monitoring or therapy within the body lumen. The invention thereby eliminates prolonged attachment of an intra-luminal medical device for a long period of time beyond a desired monitoring or therapy duration. Thus, if desired, the medical device may be detached immediately following acquisition of a sufficient amount of a data, or delivery of a sufficient course of therapy.

The details of one or more embodiments of the invention are set forth in the accompanying drawings and the description below. Other features, objects, and advantages of the invention will be apparent from the description and drawings, and from the claims.

DESCRIPTION OF THE PREFERRED EMBODIMENTS

Figure 1:
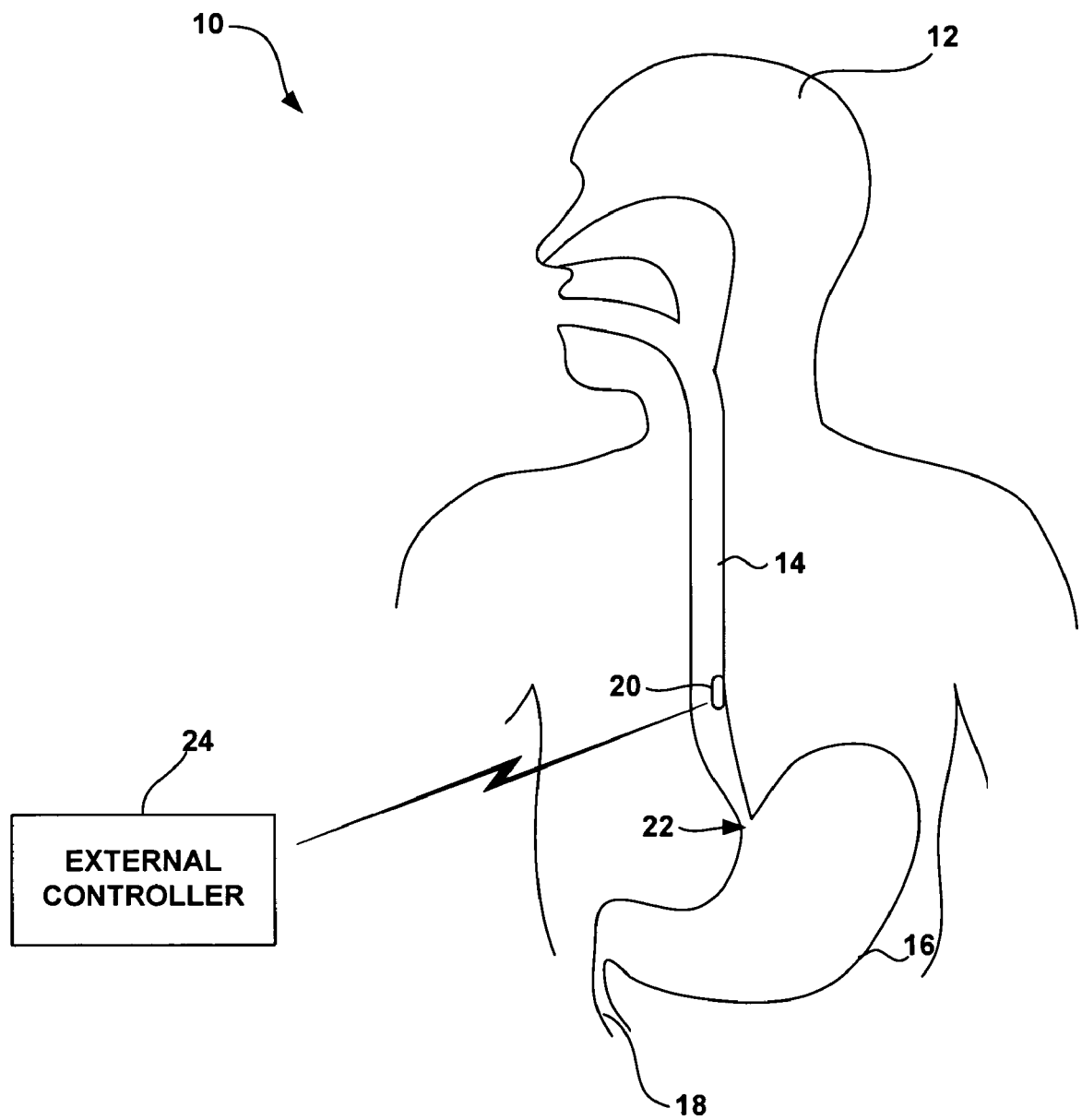
FIG. 1 is a schematic diagram illustrating an intra-luminal medical device system shown in conjunction with a patient.

FIG. 1 is a schematic diagram illustrating an intra-luminal medical device system 10 shown in conjunction with a patient 12. System 10 may be configured to monitor physiological conditions or deliver electrical stimulation at a target location within a body lumen such as the gastrointestinal tract, e.g., within esophagus 14, stomach 16 small intestine 18, or the colon (not shown). System 10 includes an implanted intraluminal medical device 20, which may be placed at the target location by endoscopic delivery. As will be described, medical device 20 includes a fixation mechanism to attach the medical device to a target tissue site, as well as a detachment mechanism that permits selective detachment of the medical device on a controlled basis. In this manner, the duration of attachment of medical device 20, and its time of release, can be controlled by medical personnel or patient 12.

Medical device 20 may be delivered via the oral or nasal passage of patient 12 using an endoscopic delivery device. In the example of FIG. 1, medical device 20 resides within esophagus 14. In this case, the endoscopic delivery device traverses esophagus 14 and then places medical device above lower esophageal sphincter (LES) 22 of patient 12, e.g., for monitoring of physiological conditions such as pressure, fluid flow, pH, or temperature to diagnose GERD. Alternatively, medical device 20 may deliver an electrical stimulation waveform to treat a variety of symptoms such as nausea, vomiting and gastric discomfort, particularly when the medical device is placed within stomach 18. In other embodiments, medical device 20 may combine both monitoring and stimulation functions. Also, medical device 20 may deliver other types of therapy in some embodiments.

Medical device 20 may have a capsule-like device housing sized for endoscopic introduction via esophagus 14 and, in some embodiments, passage through the gastrointestinal tract. For example, the capsule-like device housing of medical device 20 may have a maximum length of less than approximately 10 mm and a maximum width of less than approximately 5 mm. In some embodiments, the capsule-like device housing may be substantially cylindrical, with a length greater than its diameter and flat or rounded ends, although the invention is not limited to any particular shape. For a cylindrical device housing, medical device 20 may have a maximum height of less than approximately 10 mm and a maximum diameter of less than approximately 5 mm. The device housing may be formed from a variety of biocompatible materials such as stainless steel or titanium.

The capsule-like device housing of medical device 20 further includes a power source, a pulse generator, one or more electrodes, a fixation mechanism, and a detachment mechanism, if configured for electrical stimulation. If configured for monitoring, the capsule-like housing of medical device 20 may include a power source, a sensor, signal processing electronics, a fixation mechanism, and a detachment mechanism. Although medical device 20 may be configured for monitoring, delivery of electrical stimulation, or both, the medical device will be generally described herein in the context of monitoring.

The fixation mechanism secures medical device 20 to a target location within a body lumen such as the gastrointestinal tract. In particular, the fixation mechanism may perforate the mucosa and lodge in the muscularis externa of the gastrointestinal tract wall when introduced against the mucosa, or grip a fold of the mucosa. To place medical device 20 for gastrointestinal applications, a distal end of the endoscopic delivery device is inserted into esophagus 14 and guided to a target location within the gastrointestinal tract.

Following placement of medical device 20, the endoscopic delivery device is withdrawn from patient 12 once the medical device is attached to a target site. Hence, surgery is not required to place medical device 20 within patient 12. Moreover, following placement of medical device 20, there are no leads or other connections that extend outside of patient 12. On the contrary, medical device 20 may be entirely self-contained, self-powered and integrated within a common, capsule-like housing. In some embodiments, an external source of inductively coupled power may be used to power some features of medical device 20, such as the detachment mechanism.

The fixation mechanism may take a variety of forms, and may include a variety of features such as one or more shafts, hooks, barbs, screws, sutures, clips, pincers, staples, tacks, or other fasteners. In some embodiments, the fixation mechanism can at least partially penetrate the mucosal lining of the gastrointestinal tract. In other embodiments, the fixation mechanism pinches or otherwise holds a fold of mucosal lining tissue. In either case, the fixation mechanism securely attaches medical device 10 to the target location, subject to detachment by a controlled detachment mechanism as further described herein. Examples of suitable biocompatible materials for fabrication of the fixation mechanism include stainless steel, titanium, polyethylene, nylon, PTFE, nitinol, or the like.

In some embodiments, the fixation mechanism may be made from a degradable material that degrades or absorbs over time at the attachment site to release medical device 20 from tissue at the target location. In either case, upon detachment, medical device 20 passes through the gastrointestinal tract of patient 12. U.S. Pat. Nos. 6,285,897 and 6,698,056 to Kilcoyne et al. provide examples of fixation mechanisms for attaching monitoring devices to the lining of the esophagus, including suitable degradable materials. The fixation mechanisms described in the Kilcoyne patents may be suitable for attachment of medical device 20. The contents of the Kilcoyne et al. patents are incorporated herein by reference in their entireties.

Examples of suitable degradable materials for fabrication of the fixation mechanism or structures include bioabsorbable or dissolvable materials such as polylactic acid (PLA) or copolymers of PLA and glycolic acid, or polymers of p-dioxanone and 1,4-dioxepan-2-one, as described in the Kilcoyne patents. A variety of absorbable polyesters of hydroxycarboxylic acids may be used, such as polylactide, polyglycolide, and copolymers of lactide and glycolide, as also described in the Kilcoyne patents. Other examples of degradable materials include polyether ketone (PEEK), carbohydrates or fibrin.

Alternatively, the fixation mechanism may include or take the form of a bonding agent such as a surgical adhesive that supplements the attachment made by the fixation mechanism or serves as the fixation mechanism itself. In other words, a pin, hook or other fixation mechanism may be accompanied by a bonding agent such as a biocompatible adhesive, or the adhesive may be used as the sole fixation mechanism without mechanical fasteners. Hence, the bonding agent may work alone or in combination with a mechanical fastener to form a fixation mechanism.

Examples of suitable boding agents for bonding the medical device 10 to the mucosal lining include surgical adhesive such as any of a variety of cyanoacrylates, derivatives of cyanoacrylates, or any other adhesive compound with acceptable toxicity to human intra-luminal cells that provides the necessary adhesion properties required to secure medical device 20 to the target location for a period of time sufficient for monitoring or delivery of electrical stimulation or other therapies. Adhesives may be injected or otherwise applied into the region surrounding the target location, e.g., via one or more delivery channels within the endoscopic delivery device, or carried by the medical device 20 itself.

Other examples of suitable bonding agents include biologically mediated bonding agents such as fibrin glues. Fibrin glue is a biological tissue adhesive found to be an effective sealant and topical hemostatic agent. An example of a commercially available fibrin glue is marketed as Tissucol. Fibrin glue generally includes concentrated fibrinogen and factor XII combined with thrombin and calcium to form a coagulum. This preparation stimulates the final stage of the clotting cascade, producing a fibrin clot from fibrinogen in the presence of calcium within seconds after administration of the thrombin-activating solution. Other biologically mediated bonding agents that may be suitable include glues based on collagen, albumin or gelatin.

A detachment mechanism is configured to permit medical device 20 to self-detach from the target location, i.e., without the need for endocscopic intervention. Upon detachment, for gastrointestinal applications, medical device 20 is free to pass through the gastrointestinal tract for excretion by the patient 12. In other body lumens, medical device 20 may pass with other bodily fluids or masses, or be retrieved by an endoscopic retrieval device. In each case, rather than waiting for the attachment mechanism to detach from the target tissue site, e.g., due to sloughing of tissue or slow degradation of the attachment mechanism, the detachment mechanism permits rapid and controlled detachment, either by electrical mechanical actuation, electrical destruction, rapid degradation of the fixation mechanism, or other controllable processes. The detachment mechanism will be described in greater detail below.

As further shown in FIG. 1, in some embodiments, medical device 20 may communicate with an external controller 24 via wireless telemetry. Controller 24 may permit a user to retrieve physiological information obtained by a sensor carried by medical device 20. Alternatively, in other embodiments, controller 24 may be used to activate, deactivate and adjust stimulation parameters applied by an electrical stimulator carried by medical device 20. For example, a patient 12 or other user may use controller 24 to start stimulation, stop stimulation, set stimulation duration, or adjust stimulation amplitude, frequency, pulse width and duty cycle. In addition, external controller 24 may permit a patient 12 or other user to activate the detachment mechanism within medical device 20, and thereby selectively release the medical device from the target tissue site.

Wireless telemetry may be accomplished by radio frequency communication or proximal inductive interaction of controller 24 with medical device 20. In some embodiments, telemetry for purposes of controlling the detachment mechanism may be accomplished by simply passing a magnet over medical device 20 or inductively powering the medical device via an inductive coil interface. External controller 24 may take the form of a portable, handheld device, like a pager or cell phone, that can be carried by patient 12. External controller 24 may include an antenna that is attached to the body of patient 12 at a location proximate to the location of medical device 20 to improve wireless communication reliability. Also, in some embodiments, controller 24 may receive operational or status information from medical device 20, and may be configured to actively interrogate the medical device to receive the information.

Figure 2:
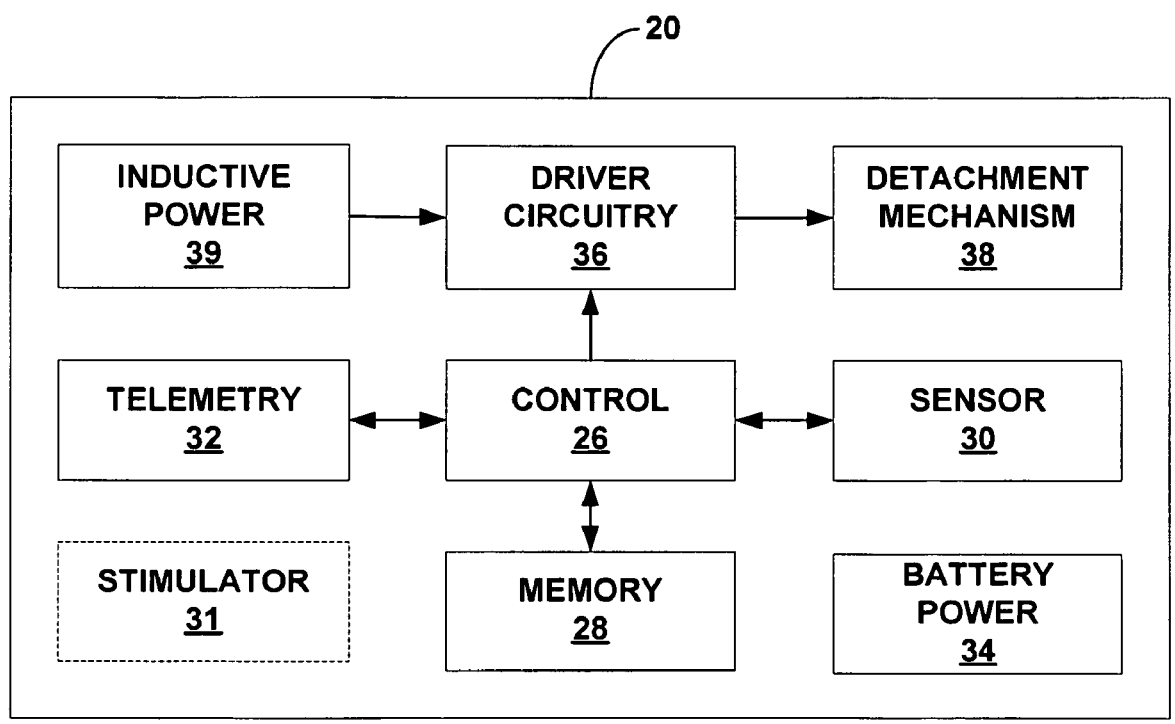
FIG. 2 is a functional block diagram illustrating exemplary components of an intra-luminal medical device.

FIG. 2 is a block diagram illustrating exemplary functional components of intra-luminal medical device 20. In the example of FIG. 2, medical device 20 may include a controller 26, memory 28, sensor circuitry 30, telemetry module 32, battery power source 34, driver circuitry 36 and detachment mechanism 38. An optional stimulator 31 is further shown in FIG. 2. In some embodiments, medical device 20 may further include an inductive power interface 39 to power driver circuitry 36 and thereby actuate detachment mechanism 38. In other embodiments, driver circuitry 36 may be powered by battery power source 34. Telemetry module 32 permits communication with external controller 24 for transfer of data. In stimulation embodiments, telemetry module 32 may be optional. For example, a medical device 20 may exclude telemetry module 32 if all operating parameters are preset and fixed within the device, or if data is to be acquired from the medical device after passage through the gastrointestinal tract. Exclusion of telemetry module 32 may be desirable in some applications to achieve reductions in the size of medical device 20.

Controller 26 controls operation of medical device 20 and may include one or more microprocessors, digital signal processors (DSPs), application-specific integrated circuits (ASICs), field-programmable gate arrays (FPGAs), or other equivalent logic circuitry. Memory 28 may include any magnetic, electronic, or optical media, such as random access memory (RAM), read-only memory (ROM), electronically-erasable programmable ROM (EEPROM), flash memory, or the like. Memory 28 may store program instructions that, when executed by controller 26, cause the controller to perform the functions ascribed to it herein. For example, memory 28 may store instructions for controller 26 to execute in support of control of telemetry module 32, sensor circuitry 30 and driver circuitry 36.

Telemetry module 32 may include a transmitter and receiver to permit bidirectional communication between medical device 20 and external controller 24. In this manner, external controller 24 may transmit commands to medical device 20 and receive status and operational information from the medical device. Telemetry module 32 includes an antenna, which may take a variety of forms. For example, the antenna may be formed by a conductive coil or wire embedded in a housing associated with medical device 20. Alternatively, the antenna may be mounted on a circuit board carrying other components of medical device 20, or take the form of a circuit trace on the circuit board. If medical device 20 does not include a telemetry module 32, a magnetic reed switch may be provided in a circuit so that medical device 20, with the aid of an external magnet, may activate itself or driver circuitry 36 and detachment mechanism 38 in response to external input.

Battery power source 34 may take the form of a battery and power circuitry. Medical device 20 typically may be used for a few days or weeks, and therefore may not require substantial battery resources. Accordingly, the battery within battery power source 34 may be very small. An example of a suitable battery is a model 317 silver oxide battery often used to power watches. The model 317 battery has voltage of 1.55 volts and a capacity of 12.5 mA-hours and has a disk-like shape with a diameter of approximately 5.7 mm and a thickness of approximately 1.65 mm. With a typical range of power requirements, the model 317 battery can be expected to power medical device 20 for between approximately two weeks and eighteen months, depending on actual usage conditions.

Different types of batteries or different battery sizes may be used, depending on the requirements of a given application. In further embodiments, battery power source 34 may be rechargeable via induction or ultrasonic energy transmission, and includes an appropriate circuit for recovering transcutaneously received energy. For example, battery power source 34 may include a secondary coil and a rectifier circuit for inductive energy transfer. In still other embodiments, battery power source 34 may not include any storage element, and medical device 20 may be fully powered via transcutaneous inductive energy transfer.

If provided, stimulator 31 incorporates a pulse generator that produces an electrical stimulation waveform with parameters selected to suppress selected symptoms, such as nausea and vomiting. Stimulator 31 may further include a charging circuit, an energy storage device to store stimulation energy, and a stimulation interface including electrodes. As an example, the pulse generator of stimulator 31 may incorporate circuitry similar to the pulse generation circuitry in the ITREL 3 neurostimulator, commercially available from Medtronic, Inc. of Minneapolis, Minn. The structure and function of stimulator 31 may generally conform to that described in commonly owned and co-pending U.S. application Ser. No. 10/801,230, to Timothy Herbert and Warren Starkebaum, filed Mar. 16, 2004, the entire content of which is incorporated herein by reference.

Figure 3:
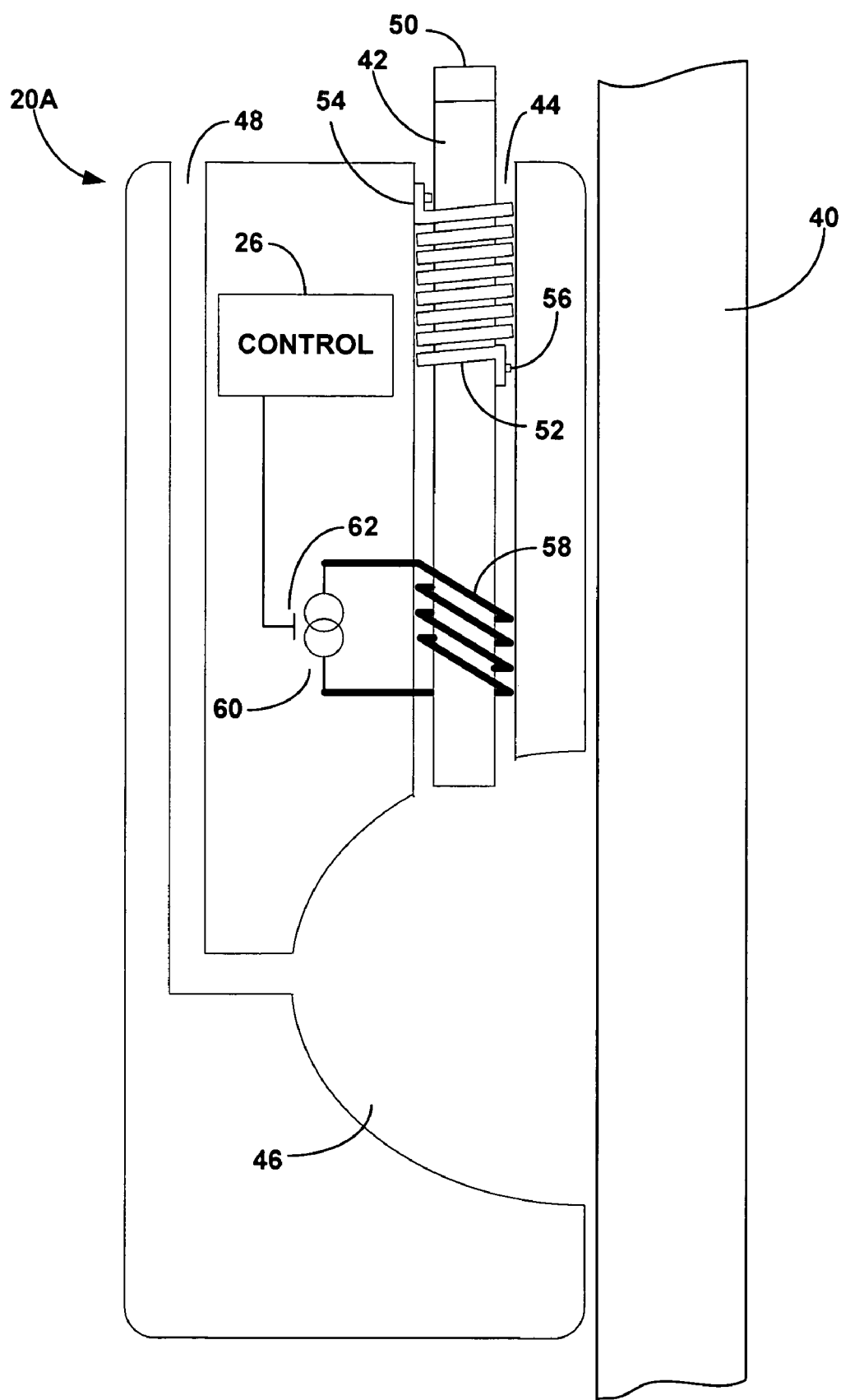
FIG. 3 is a cross-sectional side view of an intra-luminal medical device with a detachment mechanism in accordance with an embodiment of the invention.

FIG. 3 is a cross-sectional side view of an intra-luminal medical device 20A with a detachment mechanism in accordance with an embodiment of the invention. In the example of FIG. 3, medical device 20A is placed adjacent mucosal lining 40 within esophagus 14. A shaft 42 extends through an internal passage 44 in the capsule-like housing of medical device 20A. Medical device 20A defines a vacuum cavity 46 on a side of the housing adjacent mucosal lining 40. A vacuum port 48 applies vacuum pressure to vacuum cavity 46 to draw mucosal tissue into the cavity. Vacuum port 48 is attached to a vacuum line (not shown) carried by an endoscopic delivery device. A coupling member 50 is attached to a proximal end of shaft 42. An elongated control rod (not shown in FIG. 3) is mounted to coupling member 50 to hold shaft 42 in place against a mechanical bias applied by a spring 52. The elongated control rod and coupling member 50 may be coupled to one another by a threaded engagement. As will be described in further detail below, controller 26, solenoid coil 58, current source 60, and switch 62 form part of a controlled detachment mechanism.

Figure 4:
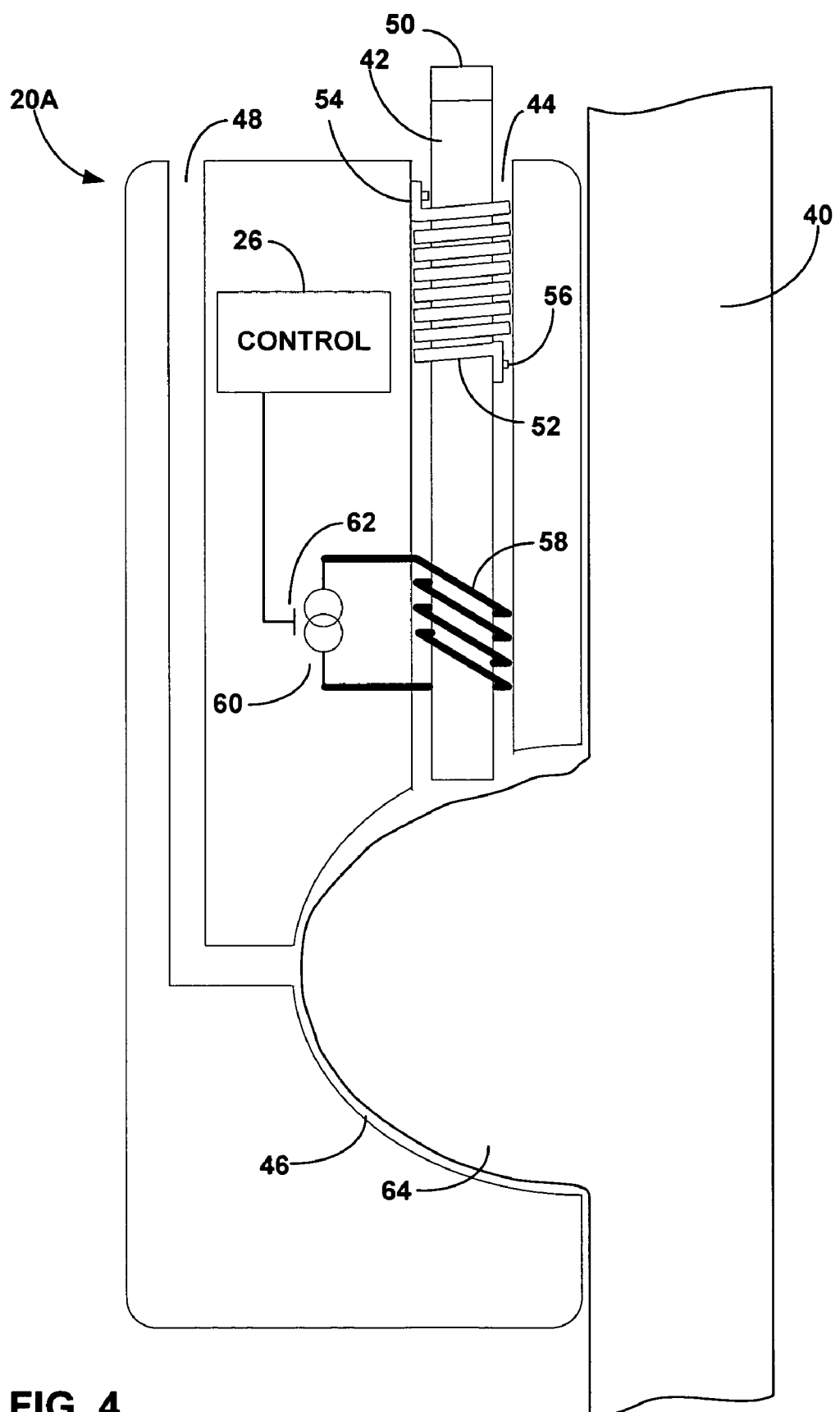
FIG. 4 is a cross-sectional side view of the medical device of FIG. 3 upon application of vacuum pressure to draw luminal tissue into the device.
Figure 5:
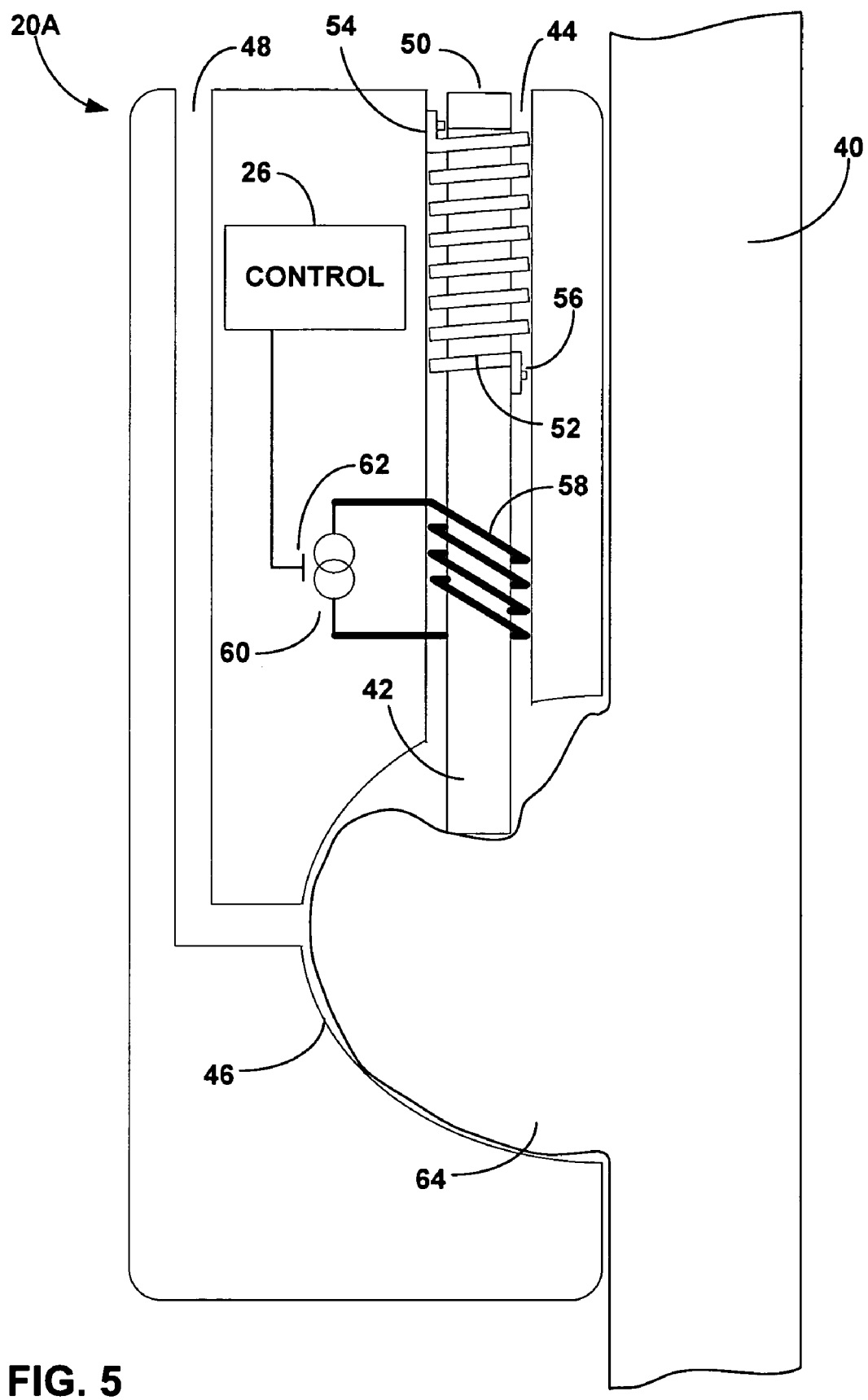
FIG. 5 is a cross-sectional side view of the medical device of FIG. 3 upon actuation of a shaft to capture luminal tissue.

FIG. 4 is a cross-sectional side view of the medical device 20A of FIG. 3 upon application of vacuum pressure via vacuum line 48 to draw mucosal tissue 64 into vacuum cavity 46 in the device. FIG. 5 is a cross-sectional side view of medical device 20A of FIG. 3 upon actuation of shaft 42 to capture mucosal tissue 64. Spring 52 is coupled at a first end 54 to medical device 20 and at a second end 56 to shaft 42. Upon release of coupling member 50 by the elongated control rod, shaft 42 extends into vacuum cavity 46 under the spring bias created by spring 52. Spring 52 biases shaft 42 against mucosal tissue 64 drawn into vacuum cavity 46 under vacuum pressure. In this manner, shaft 42 pinches mucosal tissue 64 within vacuum cavity 46, and thereby attaches medical device 20A to the mucosal lining. In other embodiments, shaft 42 may partially or completely penetrate mucosal tissue 64, and may have a sharpened tip to facilitate penetration. Vacuum pressure is then terminated, and the endoscopic delivery device is withdrawn from the esophagus, leaving medical device 20A in place.

In the example of FIGS. 3-5, shaft 42, vacuum cavity 46 and spring 52 together form a fixation mechanism that attaches medical device 20A to mucosal tissue 64 at a target site within the gastrointestinal tract. With further reference to the embodiment depicted in FIGS. 3-5, controller 26, solenoid coil 58, current source 60, and switch 62 form parts of a controlled detachment mechanism. In particular, current source 60 may form part of driver circuitry 36 (FIG. 2) to drive the detachment mechanism. Although medical device 20A could eventually detach from mucosal lining 40 due to sloughing of the tissue 64 held by shaft 42, controlled detachment is preferred so that the time of detachment, and hence the duration of implantation of the medical device within the gastrointestinal tract, can be controlled with greater certainty.

In operation, upon receipt of a control signal, controller 26 activates switch 62 to turn current source 60 "ON" and thereby drive current across solenoid coil 58. For this arrangement, shaft 42 is formed from a ferromagnetic material to magnetically interact with solenoid coil 58. Current source 60 energizes solenoid coil 58 to create a magnetic field sufficient to magnetically actuate shaft 42. In particular, solenoid coil 58 causes shaft 42 to overcome the spring bias created by spring 52 and then retract into passage 44, thereby releasing the portion of mucosal tissue 64 held within vacuum cavity 46. Once the mucosal tissue 64 is released by shaft 42, medical device 20A detaches from mucosal lining 40 for passage through the gastrointestinal tract.

Current source 60 may derive operating power from battery power source 34 (FIG. 2). Although a substantial amount of current may be required to overcome the spring bias of spring 52, the detachment mechanism only needs to be used once, i.e., at the time of detachment. Hence, battery power source 34 may be selected to provide sufficient power given the operating requirements of medical device 20A for monitoring or stimulation and the spring bias created by spring 52.

Alternatively, in some embodiments, inductive power interface 39 may be used to provide sufficient power to drive detachment mechanism 38 (FIG. 2). For example, inductive power interface 39 (FIG. 2) may be dedicated to generation of power by inductive coupling with an external source of inductive power for the purpose of driving the detachment mechanism. Inductive power interface 39 may include an inductive coil within the housing of medical device 20A for transcutaneous transfer of power from an external source.

In some embodiments, controller 26 may not be needed to drive the detachment mechanism. Instead, current source 60 may be responsive to the presence of power on a power rail due to inductive coupling of power via inductive power interface 39. In this case, power normally is not supplied to current source 60, and is only available when a patient 12 or other user presents an external power source in close proximity to inductive power interface 39 to thereby release medical device 20A.

In the examples above, the detachment mechanism may be responsive to a control signal in the form of a signal transmitted to controller 26 via telemetry module 32, or a control signal in the form of power delivered to medical device via inductive power interface 39. As a further alternative, controller 26 may be responsive to a clock carried by medical device 20A. The clock tracks a period of time from the time of deployment or activation of medical device 20A to a desired time of detachment. When the time of detachment is reached, controller 26 responds to the clock by activating the detachment mechanism. In other embodiments, controller 26 may activate the detachment mechanism when a sufficient amount of data has been obtained, or a sufficient amount of stimulation has been provided.

Figure 6:
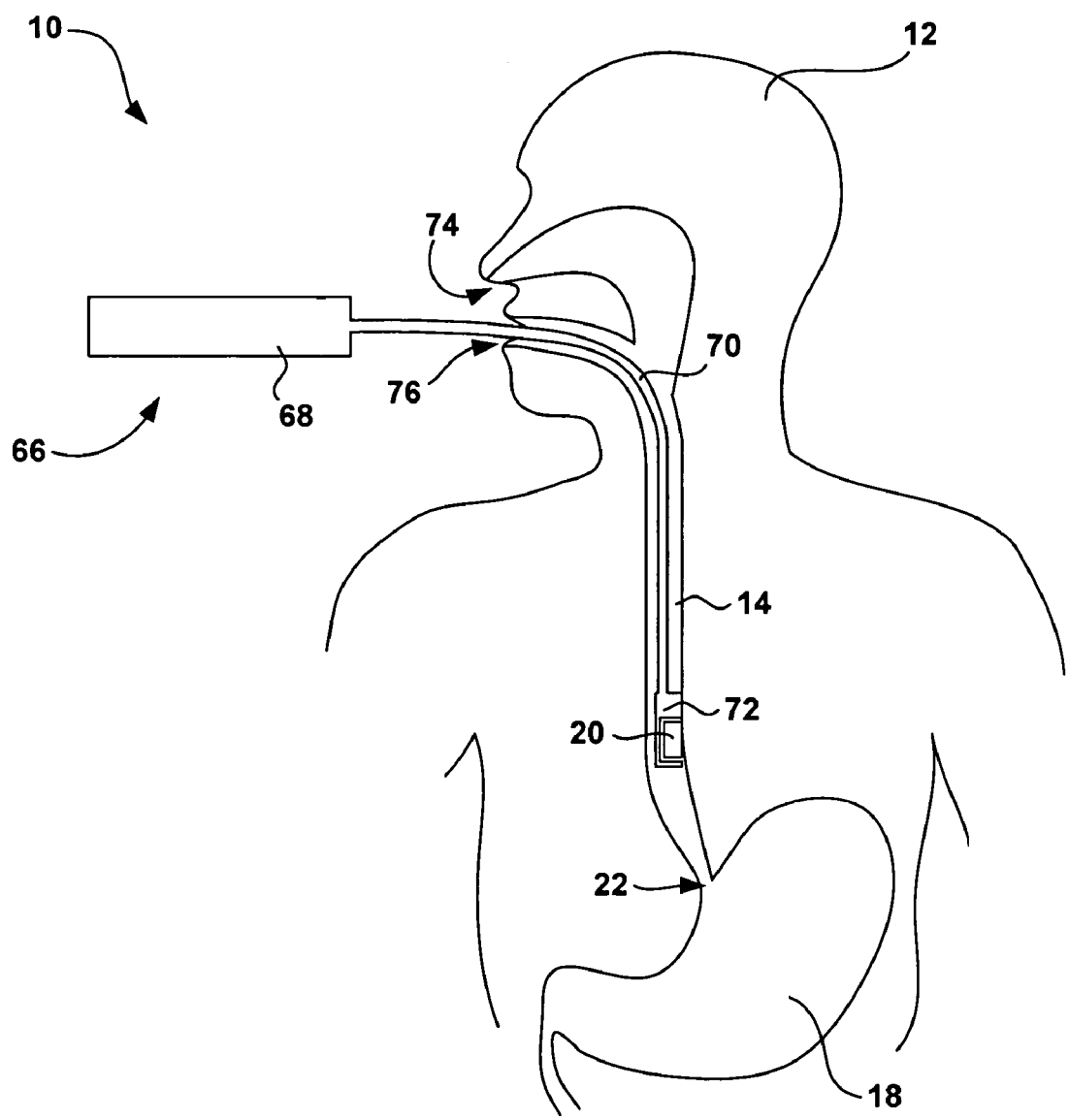
FIG. 6 is a schematic diagram illustrating deployment of the medical device of FIG. 3 within a patient's gastrointestinal tract.

FIG. 6 is a schematic diagram illustrating deployment of a medical device 20 within a patient's gastrointestinal tract. As shown in FIG. 6, an endoscopic delivery device 66 serves to position and place medical device 20 within the gastrointestinal tract of patient 12. Delivery device 66 includes a proximal portion, referred to herein as a handle 68, and a flexible probe 70 that extends from handle 68 into the gastrointestinal tract of patient 12. Medical device 20A is coupled to a distal end 72 of delivery device 66 for delivery to a target location within the gastrointestinal tract. Distal end 72 of delivery device 66 enters esophagus 14, via either nasal cavity 74 or oral cavity 76, and extends into esophagus 14 to a desired placement location. Medical device 20A is attached to the mucosal lining at a target location within esophagus 14, stomach 16 or small intestine 18, and the distal end 72 of delivery device 66 releases medical device 20A.

Figure 7:
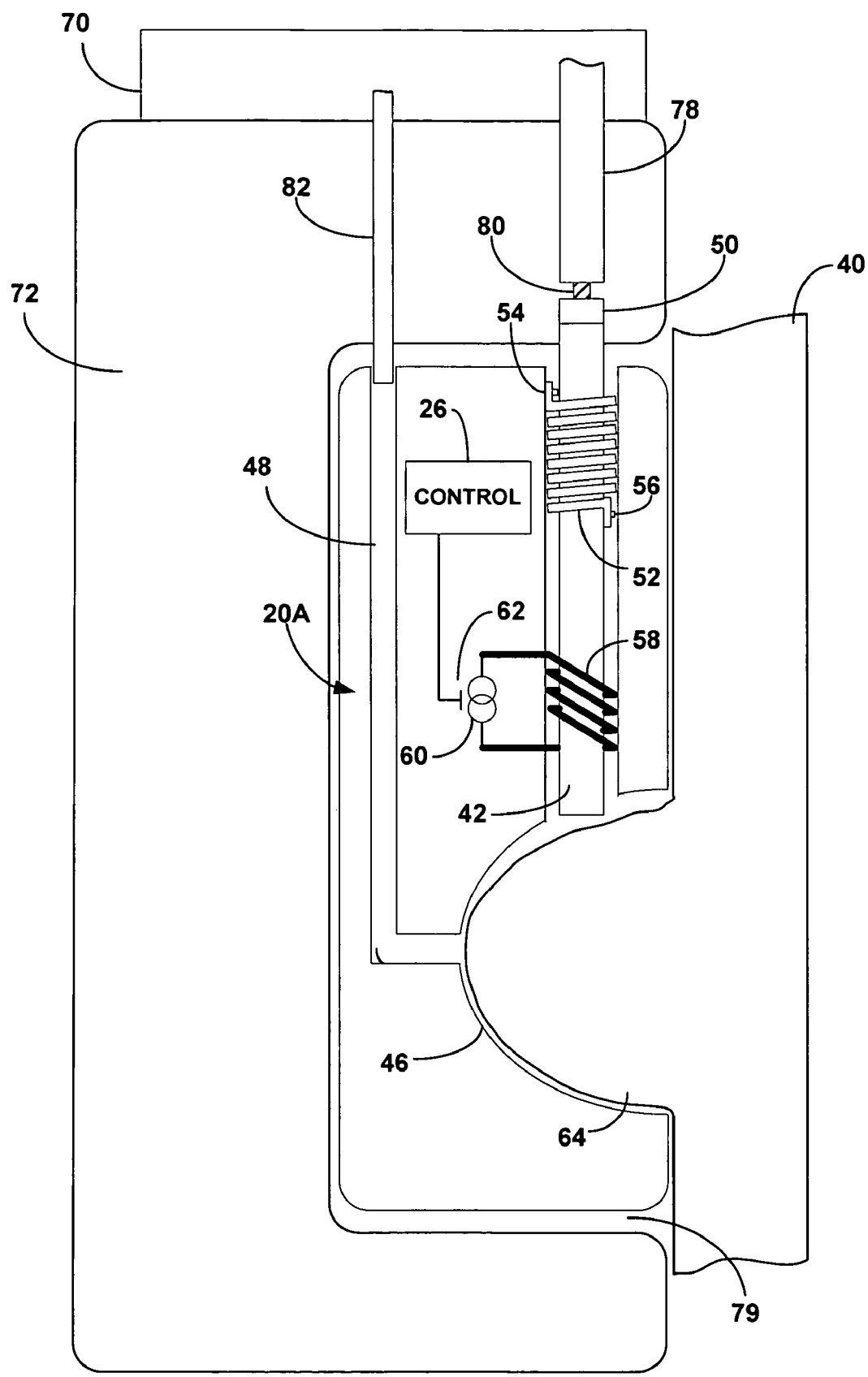
FIG. 7 is a cross-sectional side view illustrating positioning of the medical device of FIG. 3 with an endoscopic delivery device.

FIG. 7 is a cross-sectional side view illustrating positioning of medical device 20A of FIG. 3 with an endoscopic delivery device 66. As shown in FIG. 7, medical device 20A is held within a placement bay 79 within distal end 72 of endoscopic delivery device 66. In this example, an elongated control rod 78 includes a threaded member 80 that engages a reciprocally threaded bore within coupling member 50. Other types of coupling engagements may be used to attach elongated control rod 78 to coupling member 50.

In general, elongated control rod 78 permits a physician to exert force to maintain shaft 42 in a retracted position relative to vacuum cavity 46, despite the spring bias exerted in the opposite direction by spring 52. Elongated control rod 78 is flexible and extends though flexible probe 70 to handle 68 (FIG. 6) so that the physician can manipulate the elongated control rod. In particular, the physician may rotate elongated control rod 78 to withdraw the elongated control rod from threaded engagement with coupling member 50 and thereby release shaft 42 to extend into vacuum cavity 46 under spring bias supplied by spring 52.

Before releasing shaft 42, however, the physician activates vacuum line 82 to supply vacuum pressure to vacuum port 48 of medical device 20A. The vacuum pressure is applied to vacuum cavity 46 to draw mucosal tissue 64 into the vacuum cavity. Upon release of shaft 42, mucosal tissue 64 is held securely within vacuum cavity, thereby securely attaching medical device 20A to mucosal lining 40 at the desired target tissue location. The spring bias from spring 52 maintains the position of shaft 42, so that the shaft effectively pinches the mucosal tissue 64.

Figure 8:
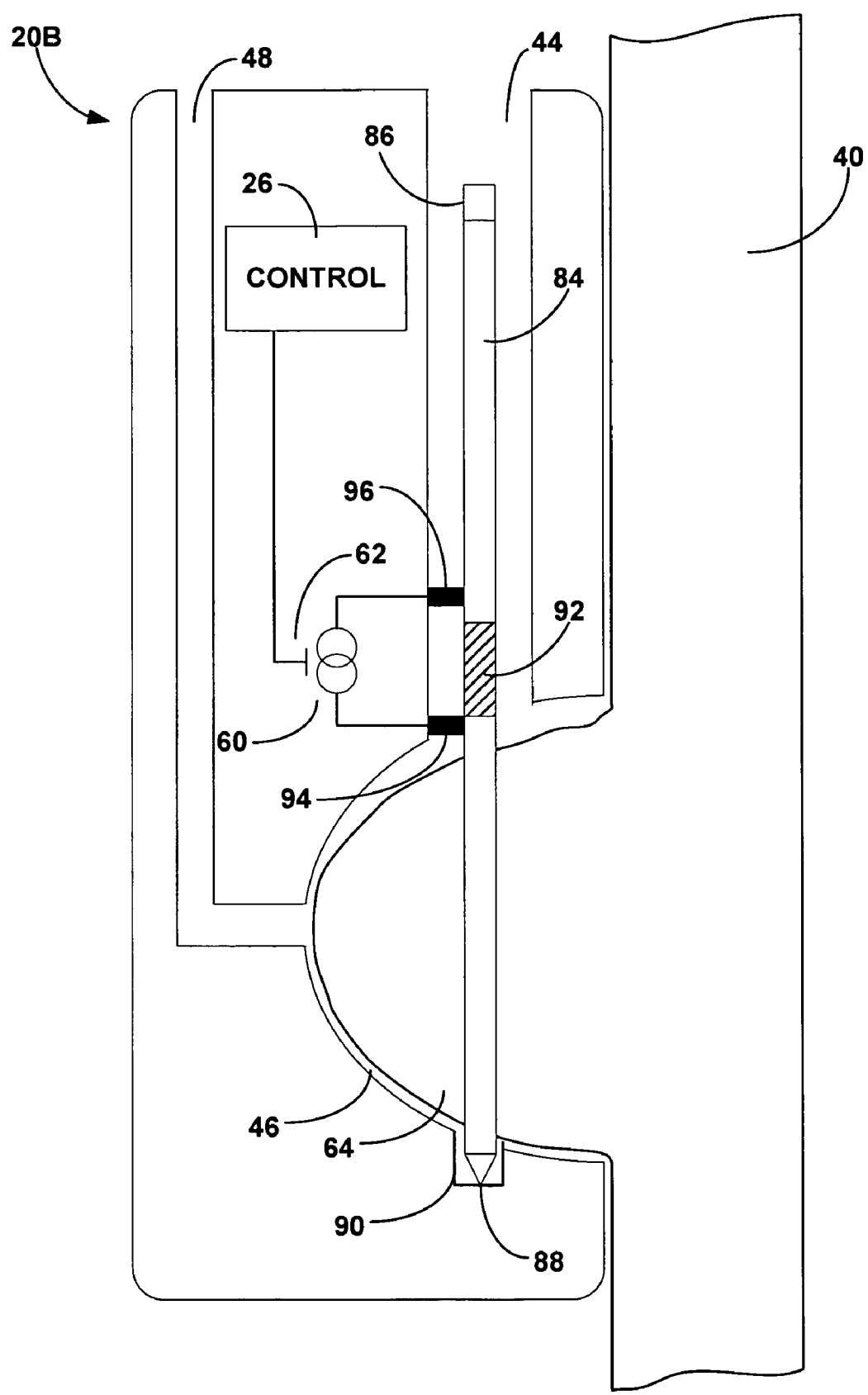
FIG. 8 is a cross-sectional side view of a medical device with a detachment mechanism including a fuse link in accordance with another embodiment of the invention.

FIG. 8 is a cross-sectional side view of an alternative medical device 20B with a detachment mechanism including a fuse link 92 in accordance with another embodiment of the invention. Medical device 20B generally conforms to medical device 20A of FIGS. 3-5 and 7. For example, medical device 20B of FIG. 8 includes passage 44, vacuum cavity 46, vacuum port 48. However, passage 44 contains a pin-like shaft 84 with a coupling member 86 and a sharpened tip 88. A physician advances an elongated control rod (not shown in FIG. 8) within an endoscopic delivery device to drive shaft 84 into and through mucosal tissue 64 captured within vacuum cavity 46 upon application of vacuum pressure. Sharpened tip 88 penetrates tissue 64 and resides in a recess 90 defined by medical device 20B. In this manner, shaft 84 securely retains mucosal tissue 64 within vacuum cavity 46, and thereby attaches medical device 20B to mucosal lining 50. In other embodiments, shaft 84 may be configured to pinch, rather than penetrate, mucosal tissue 64.

To selectively detach medical device 20B from mucosal lining 40 in a controlled manner, medical device 20B includes a detachment mechanism. The detachment mechanism includes controller 26, current source 60, switch 62, fuse link 92, and contact terminals 94 and 96. In response to a control signal, controller 26 activates switch 62 to apply current from current source 60 across contact terminals 94, 96. Again, the control signal may be delivered by an external controller, delivered in the form of power inductively transferred to the medical device 20B, or be generated in response to a clock carried by the medical device. Contact terminals 94, 96 may take the form of conductive rails, posts, brushes, or the like, which make electrical contact with shaft 84. In some embodiments, contact terminals 94, 96 may be substantially annular and extend about the circumference of shaft 84.

Shaft 84 is constructed from an electrically conductive material so that current applied across contact terminals 94, 96 is likewise applied across fuse link 92. Fuse link 92 may be constructed from any of a variety of materials that are easily degraded upon application of a sufficient level of electrical current. The fuse materials may be vaporized or melted. Example materials include nickel/chromium (nichrome), zinc/copper, or silver/copper alloys which are commonly used in fuse applications. Other possible fuse materials include polysilicon or conductive polymers or materials that contain carbon black. As further examples, a material in combination with an embedded conductive/resistive material may be used as fuse material. The embedded conductive/resistive material may be a conductive wire filament. When the wire filament heats, the surrounding material melts, causing the link to lose its mechanical strength such that the capsule dislodges from the tissue site. For example, a fuse material made of a plastic or polymer may dissolve, break, change elasticity, or otherwise change state when heat is generated by current flowing through the embedded wire filament. A fuse material can be formed as an integral part of shaft 84 with conductive proximal and distal shaft portions by molding, casting, welding, soldering or the like.

Figure 9:
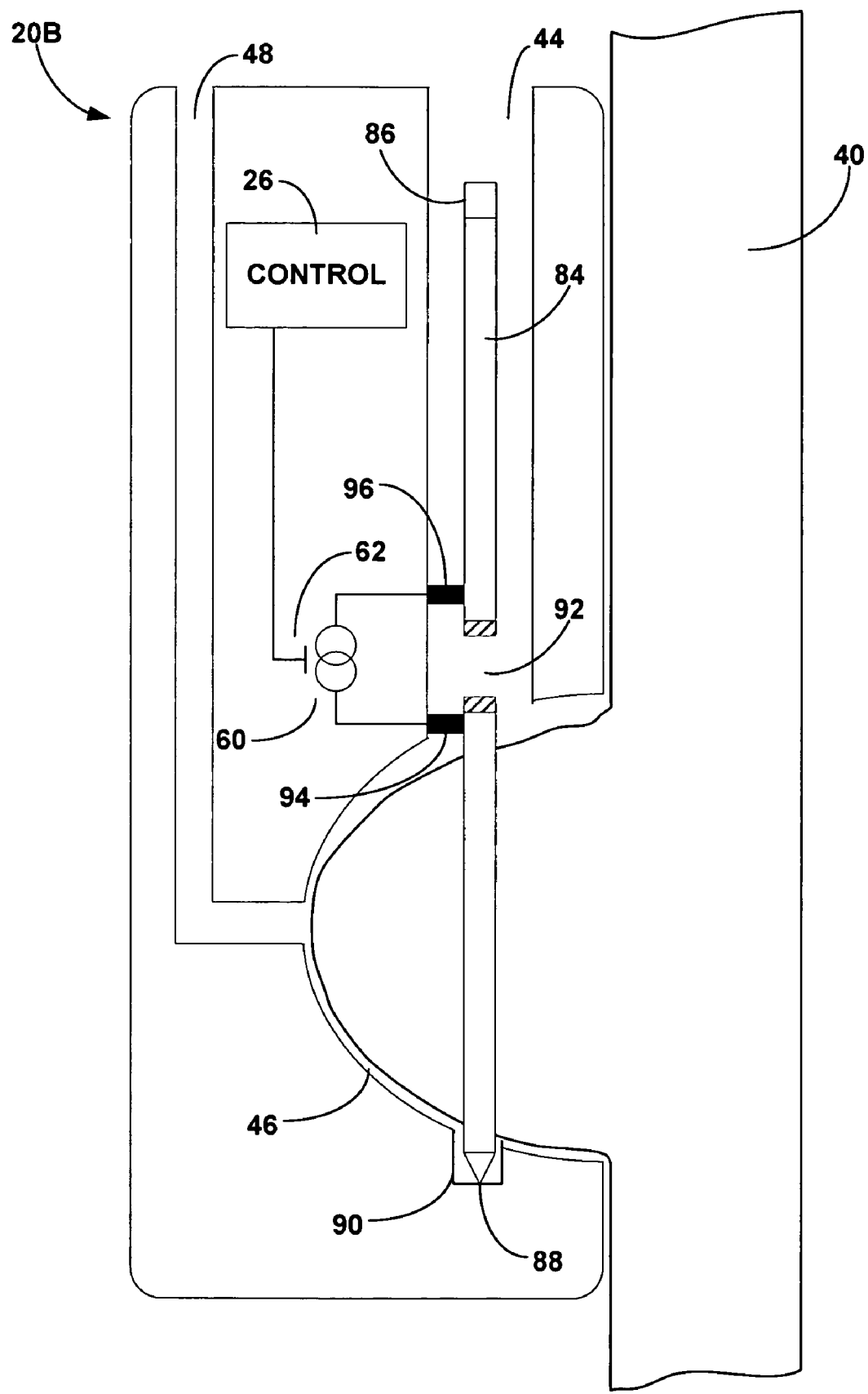
FIG. 9 is a cross-sectional side view of the medical device of FIG. 8 after the fuse link is blown by electrical current.

The electrical current from current source 60 has an amplitude level sufficient to "blow" fuse link 92, so that shaft 84 breaks apart into two or more pieces. As an example, a current level on the order of approximately 1 milliamps to approximately 500 milliamps should be sufficient to blow fuse link 92, although sufficient current levels will vary as a function of the material selected and the resistance of the material. In some embodiments, higher current levels up to approximately 20 amps may be produced for some materials. FIG. 9 is a cross-sectional side view of the medical device 20B of FIG. 8 after fuse link 92 is blown by electrical current. Once fuse link 92 is blown, medical device 20B is free to release from tissue 64. A distal portion of shaft 84 may remain in tissue 64, but eventually pass through the system of the patient as the tissue sloughs away over time.

Again, as in other embodiments, the current supplied by current source 60 may be derived from a battery power source that supplies power from a battery carried by medical device 20B, or an inductive power source that receives inductively coupled power from a power source external to the patient. Battery power may be sufficient, particularly because the level of current sufficient to blow fuse link 92 only needs to be applied once during the operational life of medical device 20B.

Figure 10:
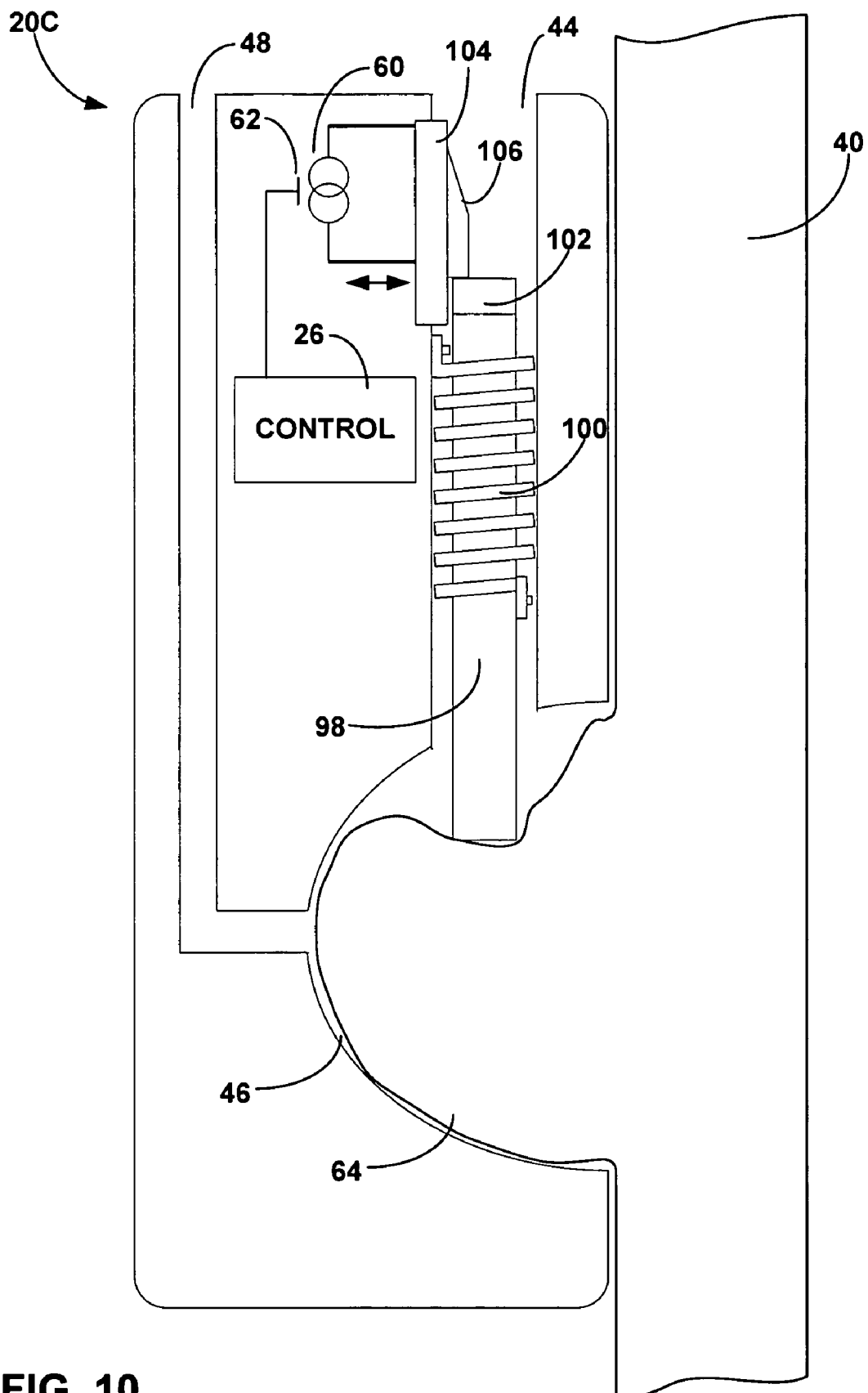
FIG. 10 is a cross-sectional side view of a medical device with a detachment mechanism including a detent actuated by a piezoelectric element in accordance with another embodiment of the invention.

FIG. 10 is a cross-sectional side view of a medical device 20C with a detachment mechanism including a detent 104 actuated by a piezoelectric element 106 in accordance with another embodiment of the invention. Like medical device 20A of FIGS. 3-5 and 7, medical device 20C includes a shaft 98 and a spring 100 that biases the shaft. However, spring 100 is configured to bias shaft 98 away from vacuum cavity 46 such that the shaft is retracted into passage 44. A detent 106 attached to a piezoelectric element 104 abuts a proximal end of shaft 98 adjacent coupling member 102, and prevents shaft 98 from retracting fully into passage 44.

During deployment, shaft 98 may be fully retracted into passage 44, such that coupling member 102 resides on a side of piezoelectric element 104 opposite spring 100. To attach medical device 20C to mucosal lining 40, a physician advances shaft 98 toward vacuum cavity 46 using an elongated control rod in the endoscopic delivery device. Upon advancement of shaft 98, coupling member 102 clears detent 106 which includes a ramped surface to facilitate clearance.

Detent 106 may be spring-loaded such that shaft 98 urges the detent outward as the shaft passes. Once coupling member 102 clears detent 106, the detent moves inward, e.g., under spring bias, to abut coupling member 102 and lock shaft 98 against movement away from vacuum cavity 46. In this manner, shaft 98 engages mucosal tissue 64 and is locked into place to secure medical device 20C against movement and thereby attach the medical device to mucosal lining 40.

In this embodiment, the detachment mechanism includes controller 26, current source 60, switch 62, and piezoelectric element 104. In response to a control signal, controller 26 activates switch 62 to cause current source 60 to supply current to piezoelectric element 104. Again, current can be derived from a battery power source or inductive power. Piezoelectric element 104 then actuates detent 106 to permit shaft 98 to clear the detent and move under the spring bias of spring 100. As alternatives, instead of piezoelectric element 104, a solenoid or other type of actuator, a fusible link, or bio or agent degradable medium can be used to release the detent 106 from shaft 98. In some embodiments, detent 106 may be formed from a degradable or fusible material. In each case, the mechanism for releasing the detent 106, and thereby releasing the mucosal tissue, is controllable.

Figure 11:
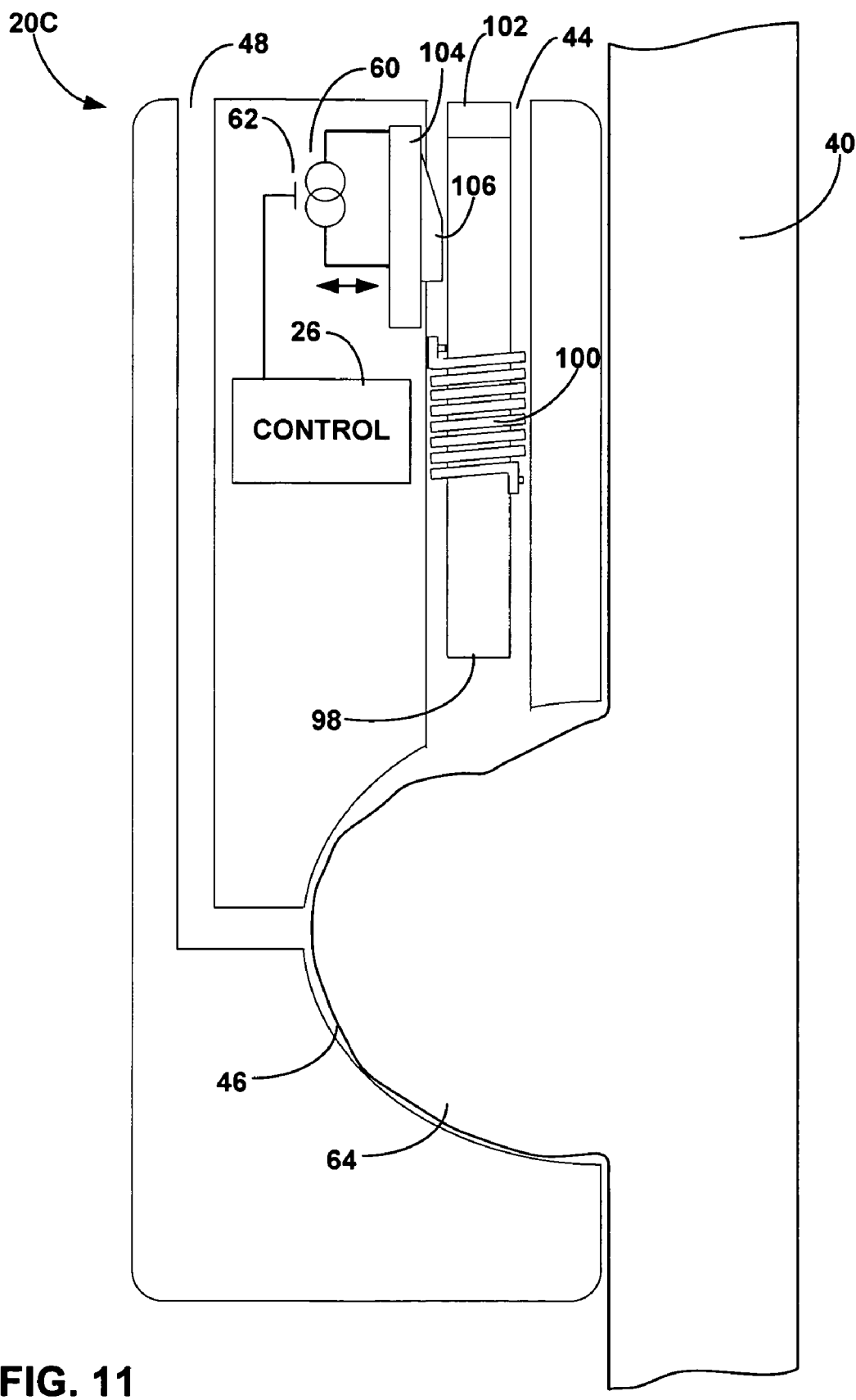
FIG. 11 is a cross-sectional side view of the medical device of FIG. 10 upon release of the detent.

FIG. 11 is a cross-sectional side view of medical device 20C of FIG. 10 upon release of the detent 106 from shaft 98. As shown in FIG. 11, shaft 98 is retracted into passage 44 and away from vacuum cavity 46. In this manner, shaft 98 retracts into passage 44 and releases mucosal tissue 64, thereby releasing medical device 20C from engagement with mucosal lining 40. Medical device 20C then falls away from mucosal lining 40 and passes through the gastrointestinal tract of patient 12.

Figure 12:
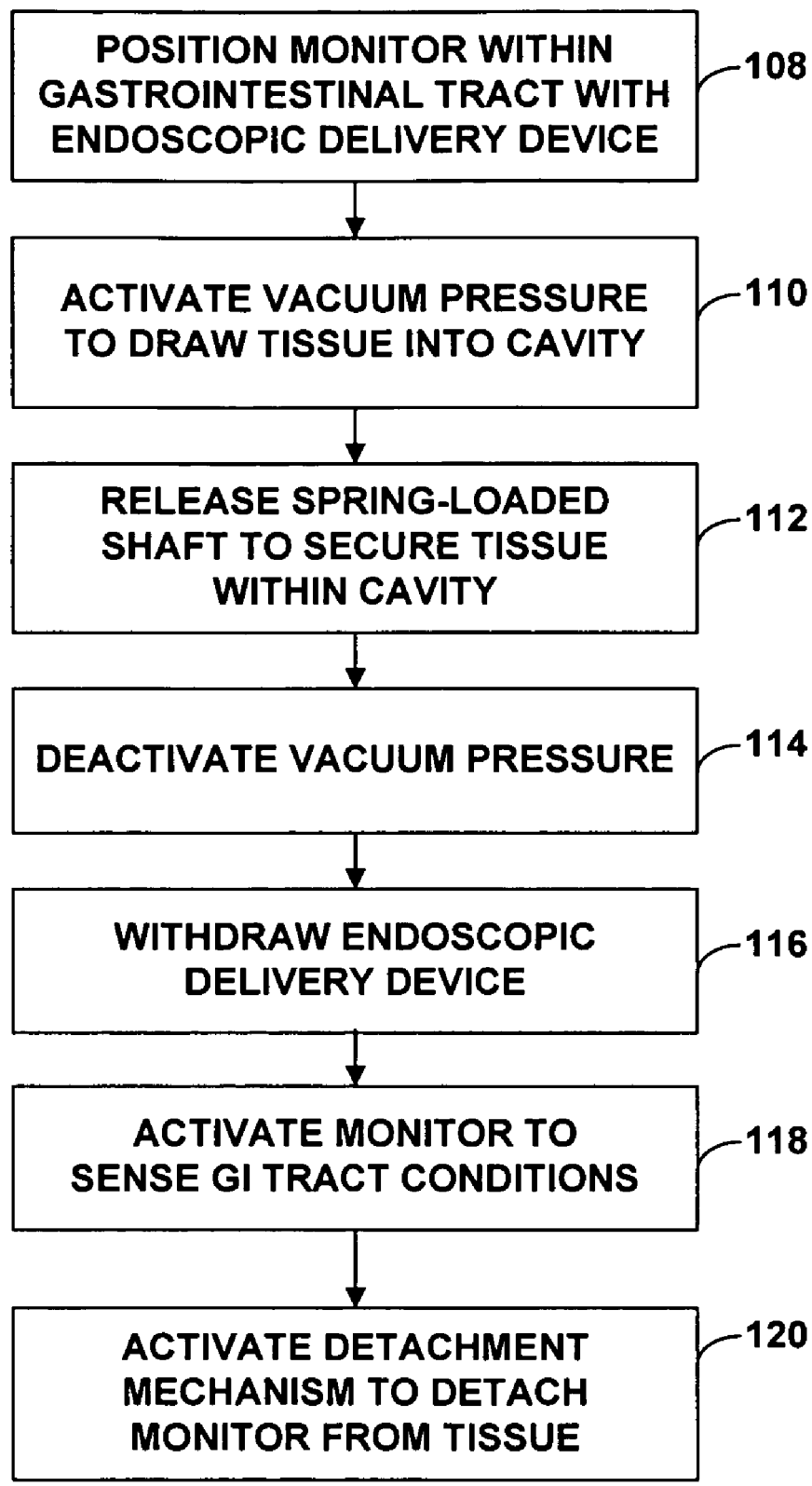
FIG. 12 is a flow diagram illustrating a method for attaching and detaching an intra-luminal medical device in accordance with an embodiment of the invention.

FIG. 12 is a flow diagram illustrating a method for attaching and detaching an intra-luminal medical device 20 in accordance with an embodiment of the invention. FIG. 12 depicts placement of a monitor device within the gastrointestinal tract for purposes of example, although the method can be used in a similar manner for other types of devices, such as electrical stimulators, as well as in other body lumens. As shown in FIG. 12, the method involves positioning a monitor within the gastrointestinal tract using an endoscopic delivery device (108), activating vacuum pressure to draw luminal tissue, e.g., mucosal tissue, into a vacuum cavity (110), and releasing a spring-loaded shaft to secure the tissue within the cavity (112). As described herein, the shaft may be a plunger-like shaft that pinches the tissue or a pin-like shaft that penetrates the tissue, either partially or completely.

As further shown in FIG. 12, upon deactivation of the vacuum pressure (114), the method involves withdrawing the endoscopic delivery device (116) from the gastrointestinal tract and activating the monitor to sense one or more physiological conditions within the gastrointestinal tract (118). After a desired monitoring time or upon completion of a desired course of treatment, in the case of a therapy device such as a stimulator, a detachment mechanism is activated to detach the device from the tissue (120), permitting the device to pass through the gastrointestinal tract. As described herein, detachment may be accomplished in a variety of ways, such as by energization of a solenoid coil, energization of a piezoelectric element, or destruction of a fuse link in the shaft.

Figure 13:
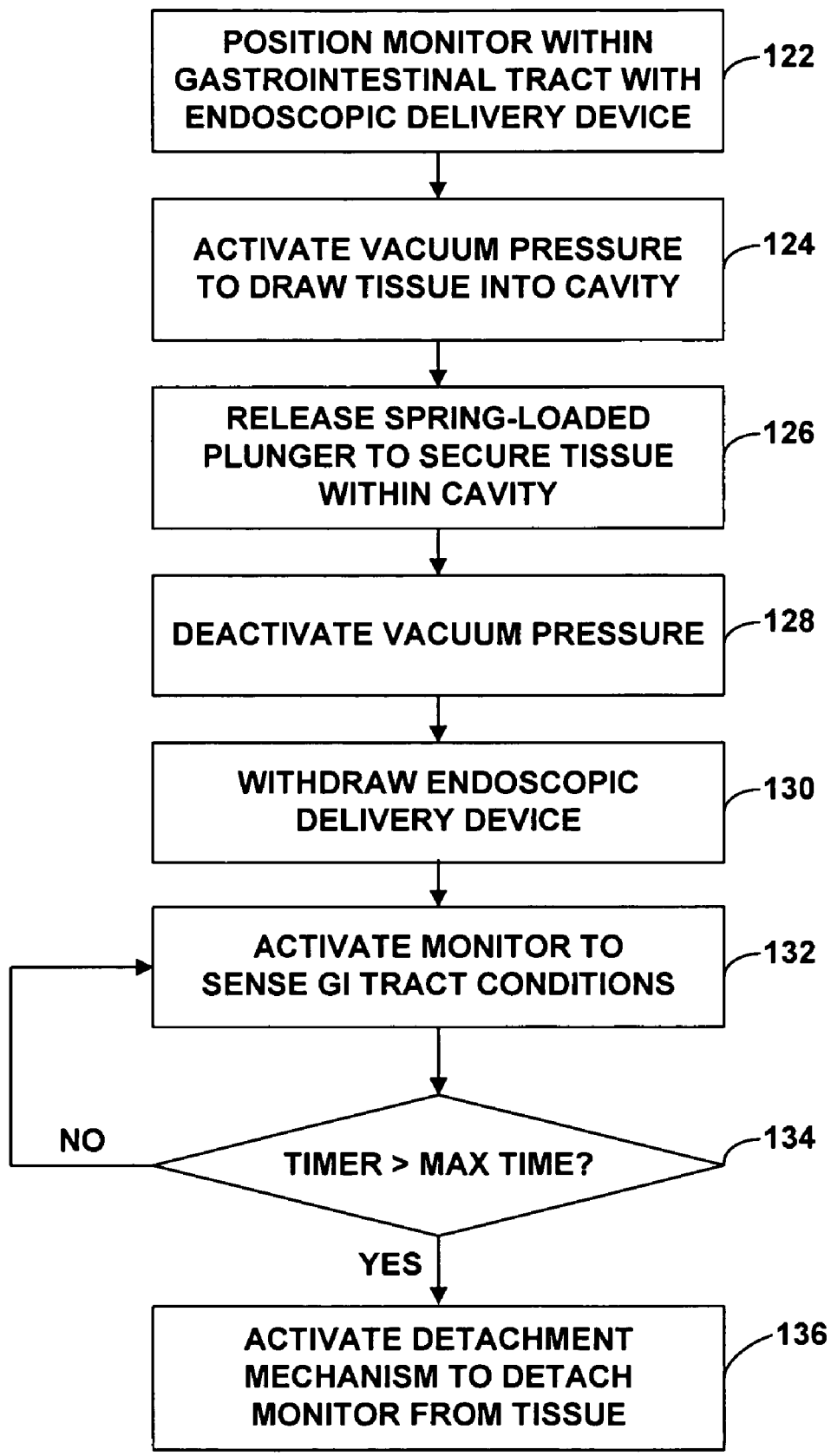
FIG. 13 is another flow diagram illustrating a method for attaching and detaching an intra-luminal medical device in accordance with another embodiment of the invention.

FIG. 13 is another flow diagram illustrating a method for attaching and detaching an intra-luminal medical device in accordance with another embodiment of the invention. Again, placement of a monitor device within the gastrointestinal tract will be described for purposes of illustration. In the example of FIG. 13, the method involves positioning a monitor within the gastrointestinal tract using an endoscopic delivery device (122), activating vacuum pressure to draw luminal tissue, e.g., mucosal tissue, into a vacuum cavity (124), and releasing a spring-loaded shaft to secure the tissue within the cavity (126). Upon deactivation of the vacuum pressure (128) and withdrawal of the endoscopic delivery device (130), the monitor is activated to sense gastrointestinal tract conditions (132), and continues to monitor the conditions until a timer maintained by a clock carried by the sensor exceeds a maximum time (134). At this point, the detachment mechanism is activated in order to detach the monitor from the mucosal tissue within the gastrointestinal tract (136).

Figure 14:
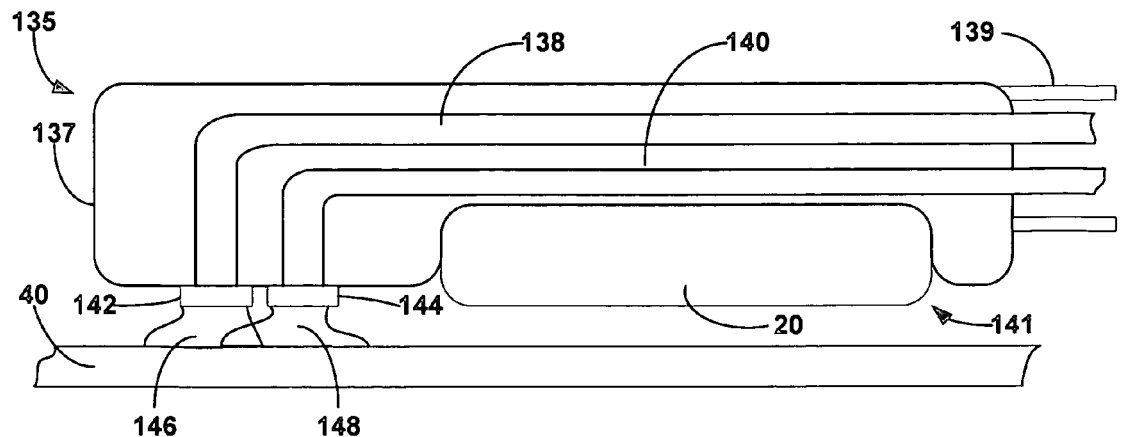
FIG. 14 is a cross-sectional side view of an endoscopic delivery device for forming a bonding agent to attach an intra-luminal medical device in accordance with an embodiment of the invention.

FIG. 14 is a cross-sectional side view of an endoscopic delivery device 135 for forming a bonding agent to attach an intra-luminal medical device 20 in accordance with an embodiment of the invention. Endoscopic delivery device 135 includes a distal end portion 137 attached to an elongated probe member 70. Medical device 20 is mounted within a placement bay 141. In the embodiment of FIG. 14, the fixation mechanism is a bonding agent that forms a bond between medical device 20 and mucosal lining 40. The bond attaches medical device 20 to a target tissue location within the body lumen. The detachment mechanism is a degradation agent that rapidly degrades the bonding agent to release medical device 20 from mucosal lining.

The bonding agent may be a surgical adhesive such as any of a variety of cyanoacrylates, derivatives of cyanoacrylates, or any other adhesive compound with acceptable toxicity to human gastrointestinal cells that provides the necessary adhesion properties required to secure medical device 20 to the target location. Adhesives may be injected or otherwise applied into the region surrounding the target location, e.g., via a one or more channel within the endoscopic delivery device 135, or carried by the medical device 20 itself.

In the example of FIG. 14, endoscopic delivery device 135 includes two delivery channels 138, 140 for delivery of constituent components 146, 148 of a bonding agent through ports 142, 144, respectively. Delivery channels 138, 140 extend along the length of elongated probe member 139 to respective sources of the constituent components at a proximal end of endoscopic delivery device 135. Constituent components 146, 148 may form parts of a two-part, cyanoacrylate-based epoxy compound. For example, one of components 146, 148 may be an epoxy resin and the other may be a hardener.

Upon introduction of components 146, 148 via ports 142, 144 of endoscopic delivery device 135, the components flow over mucosal lining 40 and mix to form a bonding agent, e.g., within a few seconds. In some embodiments, UV- or thermally-curable bonding agents may be used, in which cases endoscopic delivery device 135 may further include a UV source or heating element to cure the bonding agent. Following mixing of components 146, 148, a physician may advance endoscopic delivery device 135 so that medical device 20 is placed in contact with the resulting mixture. An endoscopic viewing device may be provided to aid in placement of medical device 20 relative to the mixture. Although FIG. 14 depicts injection of components 146, 148 via endoscopic delivery device 135, in some embodiments, medical device 20 may carry a supply of the bonding agent or constituent components, e.g., on a surface of the medical device.

Figure 15:
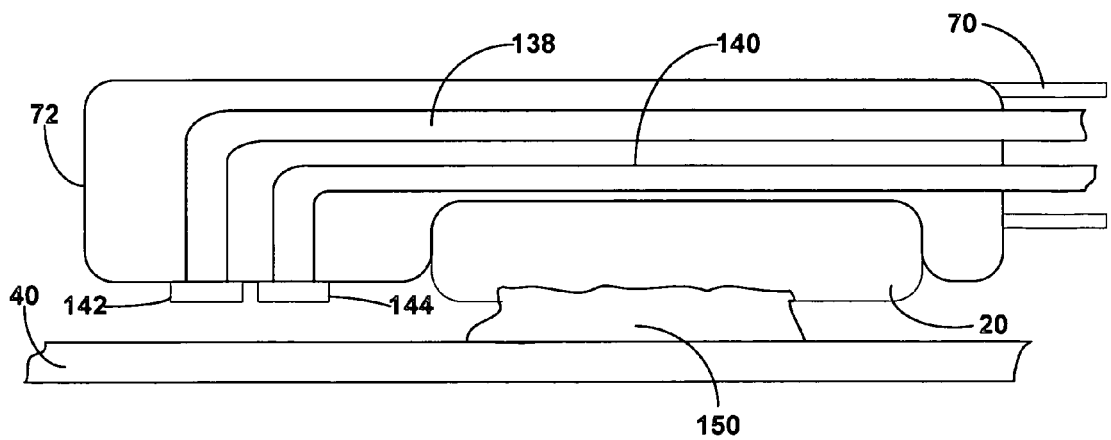
FIG. 15 is a cross-sectional side view of the endoscopic delivery device following attachment of the medical device with the bonding agent.
Figure 16:
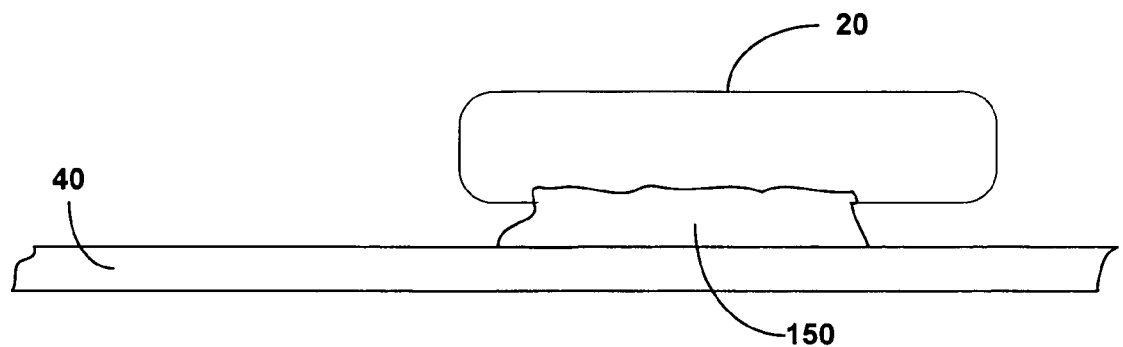
FIG. 16 is a side view of the medical device of FIGS. 14 and 15 following withdrawal of the endoscopic delivery device.
Figure 17:
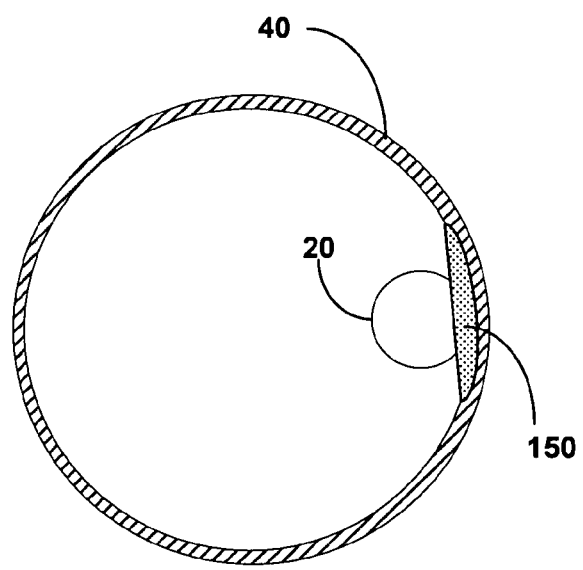
FIG. 17 is a cross-sectional end view of a body lumen in which the medical device of FIGS. 14-16 is implanted.

FIG. 15 is a cross-sectional side view of the endoscopic delivery device 135 following attachment of medical device 20 with a bonding agent 150 formed by components 146, 148. The physician releases medical device 20 either actively with a push rod or other device, or passively by pulling endoscopic delivery device 135 away from the medical device, which bonds to the bonding agent. FIG. 16 is a side view of the medical device 20 of FIGS. 14 and 15 following withdrawal of the endoscopic delivery device 135. As shown in FIG. 16, the capsule-like housing of medical device 20 remains attached to mucosal lining via bonding agent 150. FIG. 17 is a cross-sectional end view of a body lumen in which medical device 20 of FIGS. 14-16 is implanted.

In the example of FIGS. 14-17, the fixation mechanism is provided by a bonding agent. In this case, the detachment mechanism in accordance with the invention is an agent for rapidly degrading the bonding agent in order to selectively release medical device 20 from mucosal lining 40 in a controlled manner. As an example, patient 20 may ingest a selected degradation agent that travels through the body lumen in which medical device 20 is implanted. Alternatively, a degradation agent may be introduced by injection or by an endoscopic device. Examples of rapid degradation agents for a bonding agent of the type described above may include biocompatible depolymerization agents to rapidly degrade polymeric bonding agents. Examples of deployermization agents include mild acids, bases or peroxides. Another example of a rapid degradation agent is the introduction of thermal energy to melt the bonding agent. The thermal energy can be generated by the medical device 20 itself, by application of a thermal element carried by an endoscopic delivery device, by localized heating of the endoscopic delivery device with an endoscopic device, or by directed external heating such as ultrasonically generated heat. Localized heating of the medical device 20 could be accomplished by applying radio frequency (RF) current across the medical device or the bonding agent using electrodes carried by an endoscopic device.

Other examples of suitable bonding agents for use as a fixation mechanism as shown in FIGS. 14-17 include biologically mediated bonding agents such as fibrin glues. A fibrin glue, such as Tissucol, includes concentrated fibrinogen and factor XII combined with thrombin and calcium to form a coagulum. Fibrin glue may be introduced by an endoscopic delivery device 135 as shown in FIGS. 14-17 at a target tissue location. To activate the fibrin glue, endoscopic delivery device 135 may further introduce calcium so that the final stage of the clotting cascade is stimulated, producing a fibrin clot within seconds. The resulting clot securely attaches medical device 20 to mucosal lining 40.

In this embodiment, the detachment mechanism is a rapid degradation agent that breaks down the fibrin clot. For example, the patient may ingest a targeted degradation agent such as streptokinase to dissolve the clot and thereby release medical device from mucosal lining 40. Alternatively, the degradation agent may be injected or introduced by an endoscopic delivery device. A physician may supervise ingestion of the degradation agent, or the patient may simply ingest the degradation agent at a prescribed time or date.

Hence, a biologically mediated bonding agent permits secure attachment of medical device 20, as well as selective detachment on a controlled basis. Other biologically mediated bonding agents that may be suitable for this purpose include glues based on collagen, albumin or gelatin.

Figure 18:
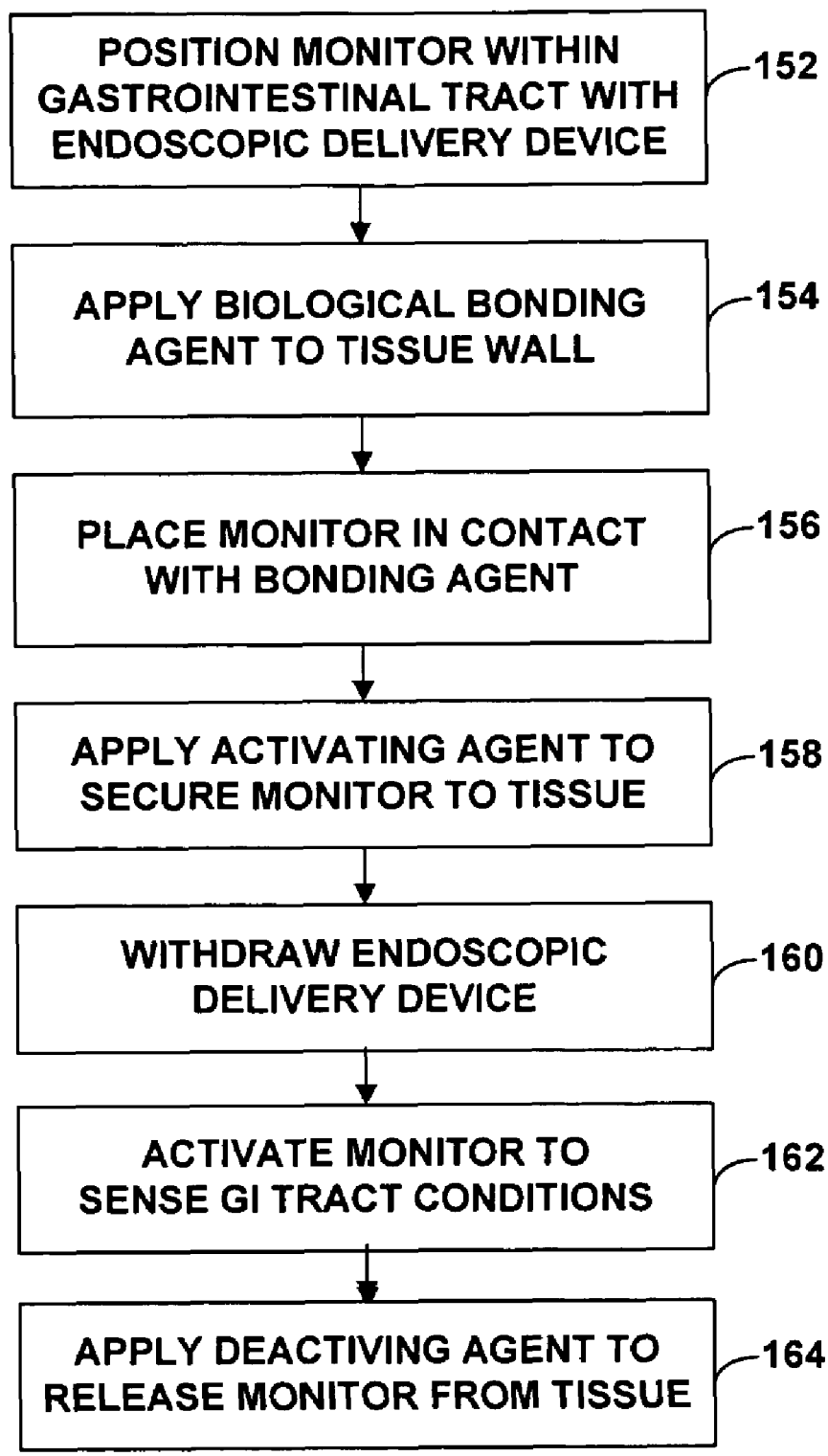
FIG. 18 is a flow diagram illustrating attachment and detachment of an intra-luminal medical device with a bonding agent and a degradation agent in accordance with an embodiment of the invention.

FIG. 18 is a flow diagram illustrating attachment and detachment of an intra-luminal medical device with a bonding agent and a degradation agent in accordance with an embodiment of the invention. Again, a monitor device and the gastrointestinal tract will be described for purposes of illustration. As shown in FIG. 18, a physician positions a monitor within the gastrointestinal tract using an endoscopic delivery device (152), applies a biological bonding agent to the tissue wall (154), and places the monitor in contact with the bonding agent (156). The physician applies an activating agent either before placement of the monitor or after placement (158). For example, constituent components of a cyanoacrylate compound may be introduced and mixed just prior to placement of the monitor, or simultaneously with placement. Alternatively, for a biologically mediated bonding agent, a patient may ingest an activating substance such as calcium upon placement of the monitor. Upon withdrawal of the endoscopic delivery device (160), the monitor is activated to sense physiological conditions within the gastrointestinal tract (162). When desired, the monitor is released from the tissue by applying a deactivating agent such as a rapid degradation agent that breaks down the bonding agent (164).

The preceding specific embodiments are illustrative of the practice of the invention. It is to be understood, therefore, that other expedients known to those skilled in the art or disclosed herein may be employed without departing from the invention or the scope of the claims. For example, the invention is not limited to deployment of a medical device at a particular location within the gastrointestinal tract. In various embodiments, a medical device may be located anywhere within the gastrointestinal tract. For example, the medical device may be affixed along or to any of the other structures and organ walls along the gastrointestinal tract, including the colon, small intestine, stomach, or the esophagus. Alternatively, the medical device may be implanted within other body lumens within a patient, such as blood vessels or the urethra.

The invention also is not limited to monitoring or electrical stimulation, but also may encompass medical devices configured to deliver different types of therapies or to serve different diagnostic purposes. In addition, the invention is not limited to application for monitoring or therapy applications associated with any particular disorder, condition or affliction.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

The invention claimed is:

1. A medical device comprising:
   a device housing sized for introduction into and residence completely within the body lumen;
   a fixation mechanism to attach the device housing to a surface within the body lumen, wherein the fixation mechanism includes a cavity formed in the device housing and a shaft to capture luminal tissue within the cavity and a spring to bias the shaft toward the tissue;
   a controlled detachment mechanism mechanically actuating the fixation mechanism to selectively detach the device housing from the surface of the body lumen without endoscopic intervention, wherein the detachment mechanism includes a solenoid coil wound about the shaft and a circuit to energize the solenoid coil to drive the shaft against the spring bias and thereby release the luminal tissue; and
   a controller responsive to a control signal, wherein the controller activates the controlled detachment mechanism, and wherein the medical device remains completely within the body lumen until after the device is detached from the surface.

2. The medical device of claim 1, wherein the cavity includes a vacuum port for application of vacuum pressure to draw the tissue into the cavity.

3. The medical device of claim 1, wherein the circuit is responsive to a control signal to energize the solenoid coil.

4. The medical device of claim 1, further comprising a power source to power the detachment mechanism.

5. The medical device of claim 4, wherein the power source includes a battery.

6. The medical device of claim 4, wherein the power source includes an inductive coupling circuit to generate power from an inductive element external to the body lumen.

7. The medical device of claim 1, wherein the controller includes a telemetry circuit to receive the control signal as a telemetry signal from an external controller.

8. The medical device of claim 1, wherein the controller includes an inductive coupling circuit to sense the presence of an external inductive element as the control signal.

9. The medical device of claim 1, wherein the controller includes an inductive coupling circuit to generate power from an inductive element external to the body lumen and thereby drive the detachment mechanism with the generated power.

10. The medical device of claim 1, wherein the device housing is sized for introduction into the esophagus.

11. The medical device of claim 1, wherein the device housing is sized for passage through the gastrointestinal tract.

12. The medical device of claim 1, further comprising a sensor, mounted to the device housing, to sense at least one condition within the body lumen.

13. The medical device of claim 1, further comprising a sensor, mounted to the device housing, to sense at least one of pH, flow, temperature, and pressure within the body lumen.

14. The medical device of claim 1, further comprising:
an electrical pulse generator, mounted within the device housing, to generate an electrical stimulation waveform;
one or more electrodes electrically coupled to the electrical pulse generator and mounted to the device housing to deliver the electrical stimulation waveform to the body lumen.

15. A method for attaching and detaching a medical device within a body lumen of a patient, the method comprising:
positioning the medical device at a target location within the body lumen;
activating a fixation mechanism carried by the medical device to attach the medical device to a surface within the body lumen wherein the fixation mechanism includes:
a cavity formed in the device housing,
a shaft to capture luminal tissue within the cavity, and
a spring to bias the shaft toward the luminal tissue, wherein activating the fixation mechanism includes advancing the shaft to capture the tissue; and
activating the fixation mechanism with a controlled mechanically actuated detachment mechanism carried by the medical device to detach the medical device from the surface of the body lumen without endoscopic intervention, wherein the detachment mechanism includes a solenoid coil wound about the shaft and wherein activating the detachment mechanism includes energizing the solenoid coil to drive the shaft against the spring bias and thereby release the luminal tissue and wherein the detachment mechanism is activated in response to receipt of a control signal from a controller external to the body lumen.

16. The method of claim 15, wherein the cavity includes a vacuum port for application of vacuum pressure to draw the tissue into the cavity, and activating a fixation mechanism includes applying vacuum pressure to the vacuum port.

17. The method of claim 15, further comprising powering the detachment mechanism with a battery carried by the medical device.

18. The method of claim 15, further comprising powering the detachment mechanism with power generated by an inductive coupling circuit carried by the medical device in response to inductive energy generated by an inductive element external to the body lumen.

19. The method of claim 15, further comprising activating the detachment mechanism in response to presence of an external magnetic source.

20. The method of claim 15, further comprising positioning the medical device within the esophagus of the patient.

21. The method of claim 15, further comprising sensing at least one of pH, flow, temperature, and pressure within the body lumen with a sensor carried by the medical device.

22. The method of claim 15, further comprising:
generating an electrical stimulation waveform; and
delivering the electrical stimulation waveform to the tissue via one or more electrodes carried by the medical device.

23. A medical device comprising:
a device housing sized for introduction into and residence completely within the body lumen;
a fixation mechanism to attach the device housing to a surface within the body lumen, wherein the fixation mechanism includes a spring to bias a shaft toward the tissue; and
a controlled detachment mechanism to selectively detach the device housing from the surface of the body lumen, wherein the detachment mechanism includes a solenoid coil wound about the shaft and a circuit to energize the solenoid coil to drive the shaft against the spring bias and thereby release the luminal tissue.

24. The medical device of claim 23, wherein the circuit is responsive to a control signal to energize the solenoid coil.

* * * * *

UNITED STATES PATENT AND TRADEMARK OFFICE
CERTIFICATE OF CORRECTION

PATENT NO. : 7,654,985 B2 Page 1 of 1
APPLICATION NO. : 10/813307
DATED : February 2, 2010
INVENTOR(S) : Dinsmoor et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 279 days.

Signed and Sealed this

Twenty-eighth Day of December, 2010

David J. Kappos
*Director of the United States Patent and Trademark Office*